US011576663B2

(12) United States Patent
Walters et al.

(10) Patent No.: US 11,576,663 B2
(45) Date of Patent: *Feb. 14, 2023

(54) VASCULAR CLOSURE DEVICE WITH REMOVABLE GUIDE MEMBER

(71) Applicant: Teleflex Life Sciences Limited, Valletta (MT)

(72) Inventors: Greg A. Walters, Exton, PA (US); Joseph Todd Grintz, Exton, PA (US); Mark Rossney, Exton, PA (US)

(73) Assignee: Teleflex Life Sciences Limited, Valletta (MT)

( * ) Notice: Subject to any disclaimer, the term of this patent is extended or adjusted under 35 U.S.C. 154(b) by 420 days.

This patent is subject to a terminal disclaimer.

(21) Appl. No.: 16/742,854

(22) Filed: Jan. 14, 2020

(65) Prior Publication Data

US 2020/0146661 A1 May 14, 2020

Related U.S. Application Data

(62) Division of application No. 15/192,632, filed on Jun. 24, 2016, now Pat. No. 10,555,727.
(Continued)

(51) Int. Cl.
*A61B 17/00* (2006.01)
*A61B 17/29* (2006.01)
*A61B 17/22* (2006.01)

(52) U.S. Cl.
CPC .. *A61B 17/0057* (2013.01); *A61B 2017/0061* (2013.01); *A61B 2017/00601* (2013.01); *A61B 2017/00623* (2013.01); *A61B 2017/00907* (2013.01); *A61B 2017/22038* (2013.01); *A61B 2017/2923* (2013.01)

(58) Field of Classification Search
CPC ...... A61B 17/0057; A61B 2017/00601; A61B 2017/0062; A61B 2017/00637; A61B 2017/22038
See application file for complete search history.

(56) References Cited

U.S. PATENT DOCUMENTS

| 3,125,095 A | 3/1964 | Kaufman et al. |
| 4,665,918 A | 5/1987 | Garza et al. |
(Continued)

FOREIGN PATENT DOCUMENTS

| EP | 0474752 B1 | 6/1995 |
| EP | 0766947 A2 | 4/1997 |
(Continued)

OTHER PUBLICATIONS

Badawi et al, "A Simple Percutaneous Technique for Hemostasis and Closure after Transcatheter Aortic Valve Implantation", Catheterization and Cardiovascular Interventions, Jan. 1, 2012, 79(1), 152-155.
(Continued)

*Primary Examiner* — Alexander J Orkin
(74) *Attorney, Agent, or Firm* — Gregory A. Grissett; Joseph P. Mathew

(57) ABSTRACT

A vascular closure device configured to seal a puncture site in the vessel wall in a more efficient manner is disclosed. The vascular closure device includes a guide member that extends through a portion of the sealing device and that is removable from the portion the sealing device.

26 Claims, 20 Drawing Sheets

Related U.S. Application Data

(60) Provisional application No. 62/185,415, filed on Jun. 26, 2015.

(56) References Cited

U.S. PATENT DOCUMENTS

| | | |
|---|---|---|
| 4,760,847 A | 8/1988 | Vaillancourt |
| 4,798,594 A | 1/1989 | Hillstead |
| 4,890,612 A | 1/1990 | Kensey |
| 4,895,346 A | 1/1990 | Steigerwald |
| 4,895,565 A | 1/1990 | Hillstead |
| 4,990,151 A | 2/1991 | Wallsten |
| 5,021,059 A | 6/1991 | Kensey et al. |
| 5,026,377 A | 6/1991 | Burton et al. |
| 5,041,095 A | 8/1991 | Littrell |
| 5,059,183 A | 10/1991 | Semrad |
| 5,222,974 A | 6/1993 | Kensey et al. |
| 5,282,827 A | 2/1994 | Kensey et al. |
| 5,292,309 A | 3/1994 | Tassel et al. |
| 5,306,254 A | 4/1994 | Nash et al. |
| 5,322,508 A | 6/1994 | Viera |
| 5,324,306 A | 6/1994 | Makower et al. |
| 5,360,414 A | 11/1994 | Yarger |
| 5,363,847 A | 11/1994 | Viera |
| 5,411,520 A | 5/1995 | Nash et al. |
| 5,531,759 A | 7/1996 | Kensey et al. |
| 5,545,178 A | 8/1996 | Kensey et al. |
| 5,643,318 A | 7/1997 | Tsukernik et al. |
| 5,662,681 A | 9/1997 | Nash et al. |
| 5,700,277 A | 12/1997 | Nash et al. |
| 5,702,421 A | 12/1997 | Schneidt |
| 5,843,124 A | 12/1998 | Hammerslag |
| 6,010,520 A | 1/2000 | Pattison |
| 6,056,768 A | 5/2000 | Cates et al. |
| 6,090,130 A | 7/2000 | Nash et al. |
| 6,107,004 A | 8/2000 | Donadio, III |
| 6,179,863 B1 | 1/2001 | Kensey et al. |
| 6,245,054 B1 | 6/2001 | Fuimaono et al. |
| 6,425,911 B1 | 7/2002 | Akerfeldt et al. |
| 6,440,151 B1 | 8/2002 | Cragg et al. |
| 6,440,153 B2 | 8/2002 | Cragg et al. |
| 6,447,534 B2 | 9/2002 | Cragg et al. |
| 6,494,848 B1 | 12/2002 | Sommercorn et al. |
| 6,682,489 B2 | 1/2004 | Tenerz et al. |
| 6,860,895 B1 | 3/2005 | Akerfeldt et al. |
| 7,037,322 B1 | 5/2006 | Sing et al. |
| 7,044,916 B2 | 5/2006 | Tenerz et al. |
| 7,073,509 B2 | 7/2006 | Tenerz et al. |
| 7,094,209 B2 | 8/2006 | Egnelov et al. |
| 7,285,097 B2 | 10/2007 | Tenerz et al. |
| 7,316,704 B2 | 1/2008 | Bagaoisan et al. |
| 7,597,705 B2 | 10/2009 | Forsberg et al. |
| 7,618,436 B2 | 11/2009 | Forsberg |
| 7,648,493 B2 | 1/2010 | Forsberg et al. |
| 7,695,493 B2 | 4/2010 | Saadat et al. |
| 7,850,654 B2 | 12/2010 | Belhe et al. |
| 7,905,902 B2 | 3/2011 | Huitema et al. |
| 8,029,533 B2 | 10/2011 | Bagaoisan et al. |
| 8,097,007 B2 | 1/2012 | Evans et al. |
| 8,137,321 B2 | 3/2012 | Argentine |
| 8,273,094 B2 | 9/2012 | Belhe et al. |
| 8,337,522 B2 | 12/2012 | Ditter |
| 8,382,793 B2 | 2/2013 | Egnelöv et al. |
| 8,435,256 B2 | 5/2013 | Lehe et al. |
| 8,444,673 B2 | 5/2013 | Thielen et al. |
| 8,540,750 B2 | 9/2013 | Tegels |
| 8,685,059 B2 | 4/2014 | Walters |
| 8,870,917 B2 | 10/2014 | Walters |
| 8,974,476 B2 | 3/2015 | Tegels |
| 9,089,363 B2 | 7/2015 | Dooney et al. |
| 9,675,371 B2 | 6/2017 | Shimon |
| 9,757,104 B2 | 9/2017 | Walters et al. |
| 10,154,835 B2 | 12/2018 | Walters et al. |
| 10,383,611 B2 | 8/2019 | Walters et al. |
| 10,390,810 B2 | 8/2019 | Walters et al. |
| 10,448,937 B2 | 10/2019 | Walters et al. |
| 10,485,524 B2 | 11/2019 | Walters et al. |
| 10,555,727 B2 | 2/2020 | Walters et al. |
| 10,639,019 B2 | 5/2020 | Walters |
| 10,668,253 B2 | 6/2020 | Jacobs |
| 10,682,128 B2 | 6/2020 | Walters et al. |
| 11,020,224 B2 | 6/2021 | Jacobs |
| 11,123,053 B2 | 9/2021 | Walters et al. |
| 11,419,592 B2 | 8/2022 | Walters et al. |
| 2001/0003158 A1 | 6/2001 | Kensey et al. |
| 2001/0044639 A1 | 11/2001 | Levinson |
| 2002/0022822 A1 | 2/2002 | Cragg et al. |
| 2003/0078616 A1 | 4/2003 | Ginn et al. |
| 2004/0138674 A1 | 7/2004 | Egnelov et al. |
| 2004/0147950 A1 | 7/2004 | Mueller et al. |
| 2004/0204741 A1 | 10/2004 | Egnelov et al. |
| 2004/0267308 A1 | 12/2004 | Bagaoisan et al. |
| 2005/0085856 A1 | 4/2005 | Ginn |
| 2005/0107820 A1 | 5/2005 | Forsberg et al. |
| 2005/0107826 A1* | 5/2005 | Zhu .............. A61B 17/0057 606/213 |
| 2005/0107827 A1 | 5/2005 | Paprocki |
| 2005/0125030 A1 | 6/2005 | Forsberg et al. |
| 2005/0277961 A1 | 12/2005 | Stone et al. |
| 2006/0058844 A1 | 3/2006 | White et al. |
| 2006/0217664 A1 | 9/2006 | Hattler et al. |
| 2006/0229673 A1 | 10/2006 | Forsberg |
| 2007/0123936 A1 | 5/2007 | Goldin et al. |
| 2007/0282373 A1 | 12/2007 | Ashby et al. |
| 2008/0082123 A1 | 4/2008 | Forsberg et al. |
| 2008/0157017 A1 | 7/2008 | Macatangay et al. |
| 2008/0306509 A1 | 12/2008 | Osborne |
| 2009/0054926 A1 | 2/2009 | Pipenhagen et al. |
| 2009/0088793 A1 | 4/2009 | Bagaoisan et al. |
| 2009/0099598 A1 | 4/2009 | McDevitt et al. |
| 2009/0137870 A1 | 5/2009 | Bakos et al. |
| 2009/0171387 A1 | 7/2009 | Pipenhagen et al. |
| 2009/0248064 A1 | 10/2009 | Preinitz |
| 2009/0312790 A1 | 12/2009 | Forsberg et al. |
| 2009/0318894 A1 | 12/2009 | Lafitte et al. |
| 2010/0016887 A1 | 1/2010 | Inderbitzi |
| 2010/0168789 A1 | 7/2010 | Bagaoisan et al. |
| 2010/0179589 A1 | 7/2010 | Roorda et al. |
| 2010/0185216 A1 | 7/2010 | Garrison et al. |
| 2011/0004162 A1 | 1/2011 | Tal |
| 2011/0046665 A1 | 2/2011 | Green et al. |
| 2011/0054456 A1 | 3/2011 | Thompson et al. |
| 2011/0160765 A1 | 6/2011 | Melmed et al. |
| 2011/0208222 A1 | 8/2011 | Ljahnicky et al. |
| 2011/0213414 A1 | 9/2011 | McGuckin, Jr. et al. |
| 2011/0213415 A1 | 9/2011 | McGuckin, Jr. et al. |
| 2011/0301619 A1 | 12/2011 | Walters |
| 2012/0010634 A1 | 1/2012 | Crabb et al. |
| 2012/0022585 A1 | 1/2012 | Atanasoska et al. |
| 2012/0065668 A1 | 3/2012 | Ginn et al. |
| 2012/0071919 A1 | 3/2012 | Pipenhagen et al. |
| 2012/0083829 A1 | 4/2012 | Ginn et al. |
| 2012/0101525 A1 | 4/2012 | Jenson et al. |
| 2012/0109192 A1 | 5/2012 | Egnelöv et al. |
| 2012/0116446 A1 | 5/2012 | Green et al. |
| 2012/0143244 A1 | 6/2012 | Hill et al. |
| 2012/0143245 A1 | 6/2012 | Tegels |
| 2012/0143249 A1 | 6/2012 | Jenson et al. |
| 2012/0158044 A1 | 6/2012 | Jenson et al. |
| 2012/0165854 A1 | 6/2012 | Pipenhagen et al. |
| 2012/0245517 A1 | 9/2012 | Tegels |
| 2012/0245597 A1 | 9/2012 | Tegels |
| 2012/0245624 A1 | 9/2012 | Glazier et al. |
| 2012/0283770 A1 | 11/2012 | Kramer et al. |
| 2012/0296275 A1 | 11/2012 | Martin et al. |
| 2013/0006297 A1 | 1/2013 | Drasler |
| 2013/0006298 A1 | 1/2013 | Terwey |
| 2013/0025588 A1 | 1/2013 | Bosel |
| 2013/0035719 A1 | 2/2013 | Hill et al. |
| 2013/0072949 A1 | 3/2013 | Halac et al. |
| 2013/0079802 A1 | 3/2013 | Halac et al. |
| 2013/0103077 A1 | 4/2013 | Ditter |
| 2013/0131718 A1 | 5/2013 | Jenson et al. |
| 2013/0144316 A1 | 6/2013 | McCrea et al. |
| 2013/0150884 A1 | 6/2013 | Belhe et al. |

(56) References Cited

U.S. PATENT DOCUMENTS

| | | |
|---|---|---|
| 2013/0178895 A1 | 7/2013 | Walters et al. |
| 2013/0226227 A1 | 8/2013 | Terwey |
| 2014/0039264 A1 | 2/2014 | Heiman |
| 2014/0046217 A1 | 2/2014 | Lim |
| 2014/0046220 A1 | 2/2014 | Nelson |
| 2014/0094846 A1 | 4/2014 | Lim et al. |
| 2014/0188160 A1 | 7/2014 | Tegels |
| 2014/0200611 A1 | 7/2014 | Walters |
| 2014/0236088 A1 | 8/2014 | Al-Rashdan et al. |
| 2014/0309686 A1 | 10/2014 | Ginn et al. |
| 2015/0068009 A1 | 3/2015 | Walters |
| 2015/0100083 A1 | 4/2015 | Walters et al. |
| 2015/0173794 A1 | 6/2015 | Kurth et al. |
| 2016/0228109 A1 | 8/2016 | Jacobs et al. |
| 2017/0135725 A1 | 5/2017 | Tegels |
| 2017/0333015 A1 | 11/2017 | Walters et al. |
| 2019/0015204 A1 | 1/2019 | Jacobs |
| 2019/0015637 A1 | 1/2019 | Jacobs |
| 2019/0110781 A1 | 4/2019 | Walters et al. |
| 2019/0336116 A1 | 11/2019 | Walters et al. |
| 2020/0000448 A1 | 1/2020 | Walters et al. |
| 2020/0289101 A1 | 9/2020 | Walters |
| 2022/0273277 A1 | 9/2022 | Walters et al. |
| 2022/0338852 A1 | 10/2022 | Walters |

FOREIGN PATENT DOCUMENTS

| | | |
|---|---|---|
| EP | 0797953 A2 | 10/1997 |
| EP | 1163020 A1 | 12/2001 |
| EP | 1169968 A1 | 1/2002 |
| EP | 1222896 A2 | 7/2002 |
| EP | 1254634 A1 | 11/2002 |
| EP | 0664687 B2 | 8/2003 |
| EP | 1371333 A1 | 12/2003 |
| EP | 1413255 A1 | 4/2004 |
| EP | 1440661 A1 | 7/2004 |
| EP | 1532929 A1 | 5/2005 |
| EP | 1658811 A1 | 5/2006 |
| EP | 1695667 A1 | 8/2006 |
| EP | 1836967 A1 | 9/2007 |
| EP | 1836968 A1 | 9/2007 |
| EP | 2055236 A1 | 5/2009 |
| EP | 2064999 A2 | 6/2009 |
| EP | 2213247 A1 | 8/2010 |
| EP | 2215974 A2 | 8/2010 |
| EP | 1919367 B1 | 10/2011 |
| EP | 1874195 B1 | 1/2012 |
| EP | 1893100 B1 | 3/2012 |
| EP | 2227148 B1 | 4/2012 |
| EP | 1893099 B1 | 6/2012 |
| EP | 1893098 B1 | 1/2014 |
| EP | 2611366 B1 | 7/2014 |
| EP | 2605707 B1 | 10/2014 |
| EP | 1773438 B1 | 1/2017 |
| WO | 1989011301 A1 | 11/1989 |
| WO | 1990014796 A1 | 12/1990 |
| WO | 1992014396 A1 | 9/1992 |
| WO | 1993008743 A1 | 5/1993 |
| WO | 1993008746 A3 | 8/1993 |
| WO | 1994007421 A1 | 4/1994 |
| WO | 1998005259 A1 | 2/1998 |
| WO | 1999022646 A1 | 5/1999 |
| WO | 2000078226 A1 | 12/2000 |
| WO | 2003094740 A1 | 11/2003 |
| WO | 2004096056 A2 | 11/2004 |
| WO | 2005002451 A1 | 1/2005 |
| WO | 2005039387 A2 | 5/2005 |
| WO | 2005060514 A2 | 7/2005 |
| WO | 2006075228 A1 | 7/2006 |
| WO | 2006110615 A2 | 10/2006 |
| WO | 2007035187 A2 | 3/2007 |
| WO | 2008036634 A1 | 3/2008 |
| WO | 2009005722 A1 | 1/2009 |
| WO | 2009025836 A1 | 2/2009 |
| WO | 2009029914 A1 | 3/2009 |
| WO | 2009035921 A2 | 3/2009 |
| WO | 2009088440 A1 | 7/2009 |
| WO | 2009088441 A1 | 7/2009 |
| WO | 2009112930 A2 | 9/2009 |
| WO | 2010129042 A1 | 11/2010 |
| WO | 2011014244 A1 | 2/2011 |
| WO | 2011019374 A1 | 2/2011 |
| WO | 2011025529 A1 | 3/2011 |
| WO | 2011025543 A2 | 3/2011 |
| WO | 2011037635 A1 | 3/2011 |
| WO | 2011146729 A2 | 11/2011 |
| WO | 2011156498 A1 | 12/2011 |
| WO | 2012009007 A1 | 1/2012 |
| WO | 2012012641 A1 | 1/2012 |
| WO | 2012045356 A1 | 4/2012 |
| WO | 2012061486 A2 | 5/2012 |
| WO | 2012064888 A2 | 5/2012 |
| WO | 2012083045 A1 | 6/2012 |
| WO | 2012145356 A1 | 10/2012 |
| WO | 2012145362 A1 | 10/2012 |
| WO | 2012148745 A1 | 11/2012 |
| WO | 2012148747 A1 | 11/2012 |
| WO | 2012158662 A1 | 11/2012 |
| WO | 2012158737 A1 | 11/2012 |
| WO | 2012158738 A1 | 11/2012 |
| WO | 2012158740 A1 | 11/2012 |
| WO | 2012158931 A1 | 11/2012 |
| WO | 2013063227 A1 | 5/2013 |
| WO | 2013081659 A1 | 6/2013 |
| WO | 2015099977 A1 | 7/2015 |
| WO | 2017123853 A1 | 7/2017 |

OTHER PUBLICATIONS

Bui et al, "Double-Wire Angio-Seal Closure Technique after Balloon Aortic Valvuloplasty", Catheterization and Cardiovascular Interventions, 2010, 75, 488-492.
Extended European Search Report and Opinion dated Jun. 16, 2021 in EP Application No. 21163623.8.
Extended European Search Report dated Sep. 6, 2021 in EP Application No. 21166157.4.
International Search Report and Written Opinion for International Application No. PCT/US2012/061855 dated Jan. 22, 2013 (21 pages).
Koh, Wui-Jin et al. "Femoral vessel depth and the implications for groin node radiation," 1993, International Journal of Radiation Oncology 'Biology' Physics, vol. 27, p. 969-974.
Officer Gunter Held, International Search Report and the Written Opinion, International Patent Application PCT/JS2017/013314, dated Apr. 18, 2017, 11 pp.
PCT International Preliminary Report on Patentability, PCT/US2014/068694, dated Jun. 28, 2016, 11 pp.
PCT International Search Report and the Written Opinion, PCT/US2014/068694, dated Mar. 17, 2015, 17 pp.
PCT International Search Report dated Oct. 22, 2021 in PCT/US2021/041730.
PCT Written Opinion dated Oct. 22, 2021 in PCT/US2021/041730.

* cited by examiner

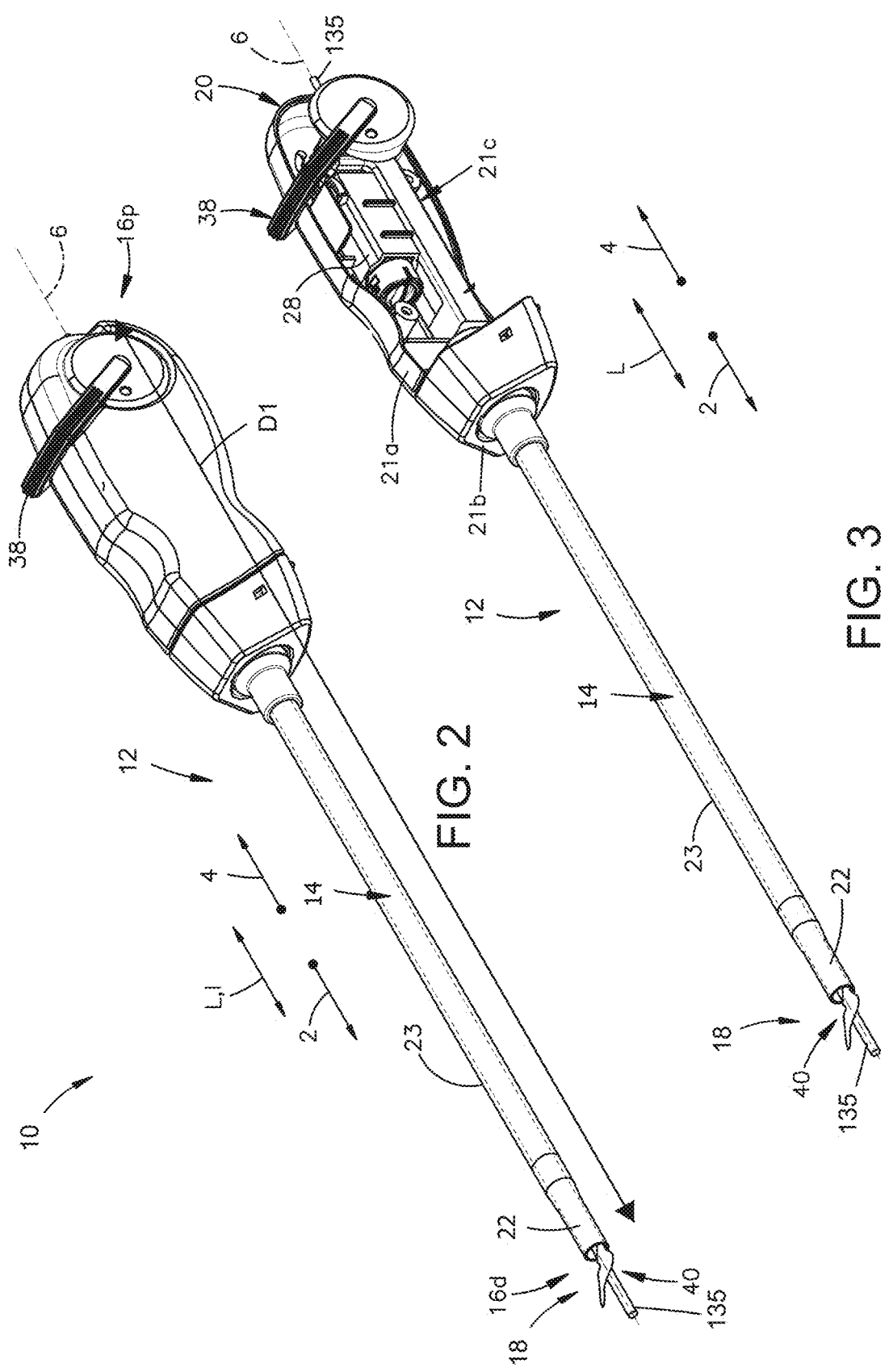

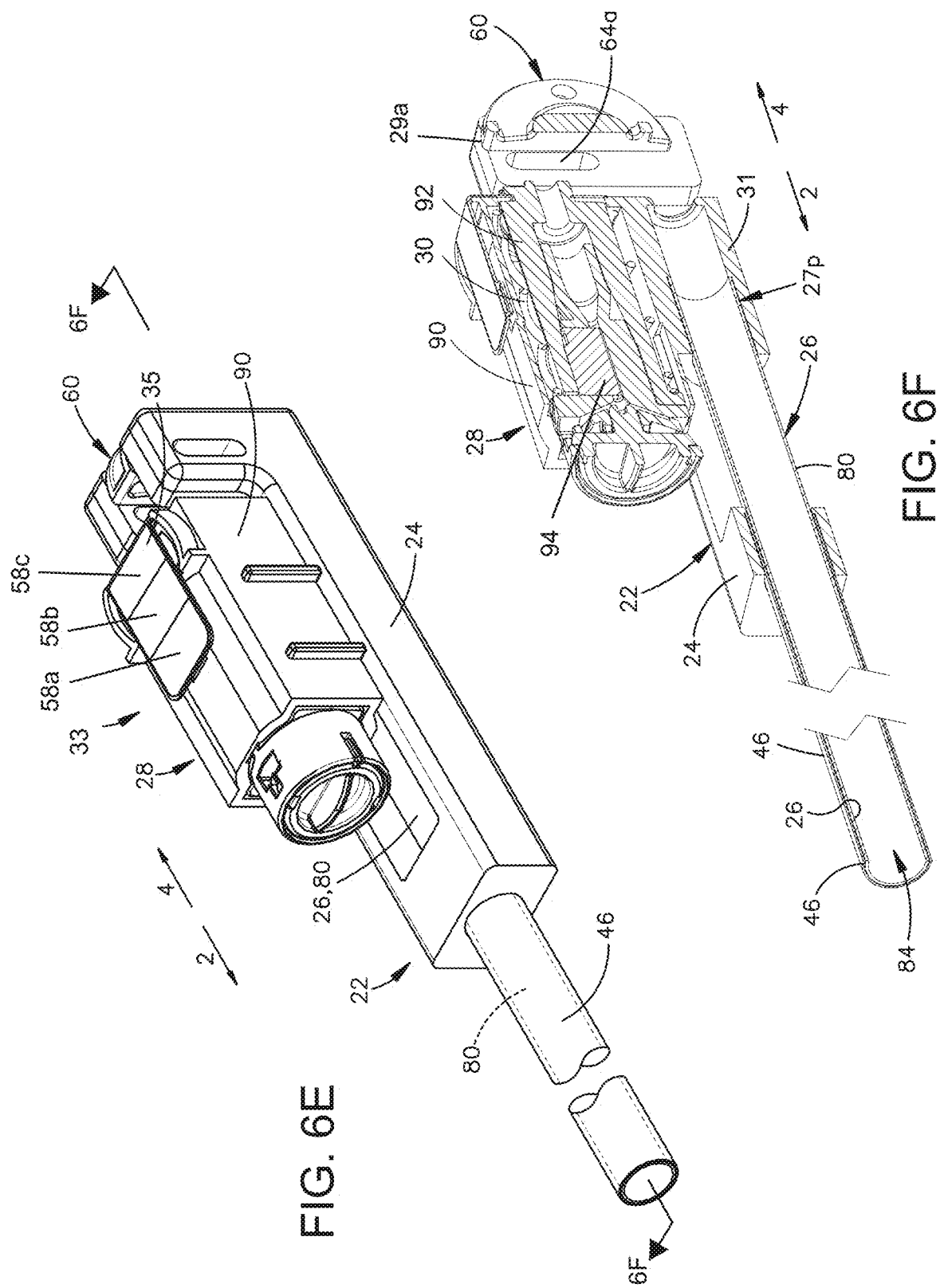

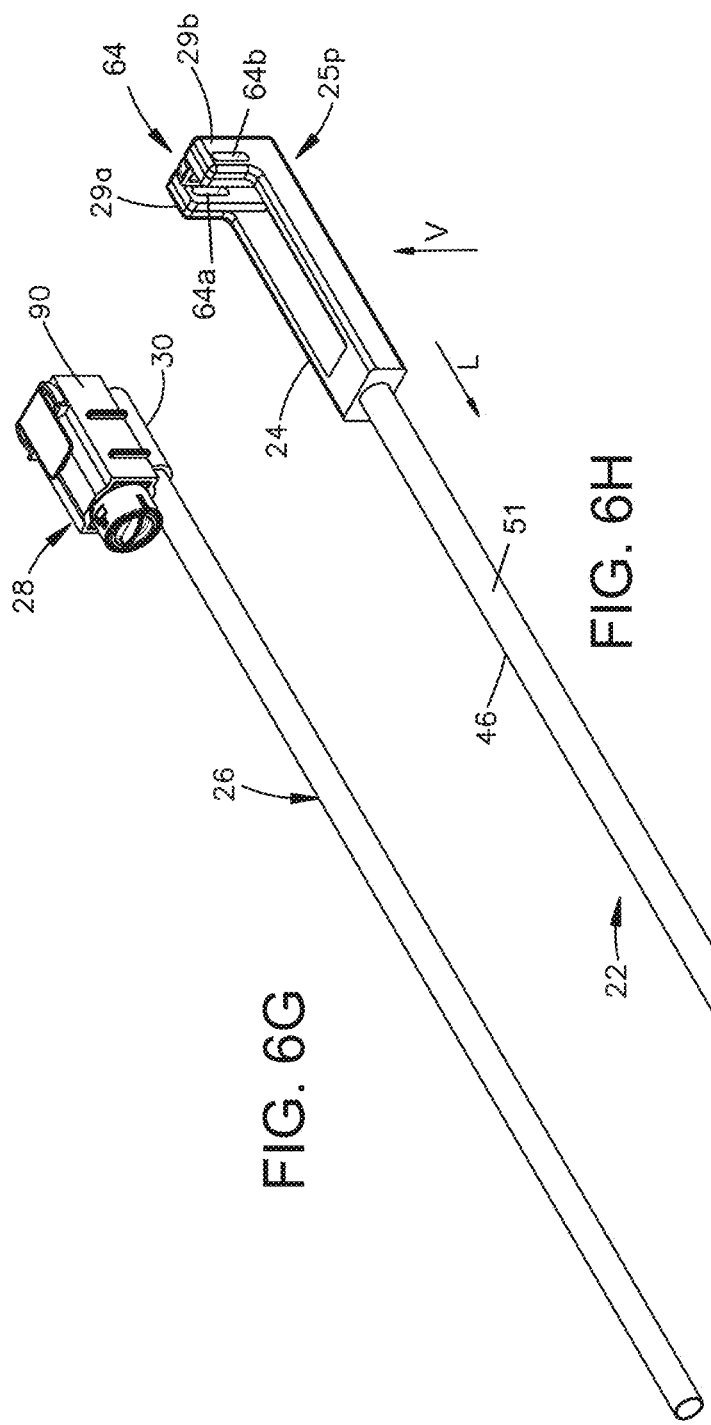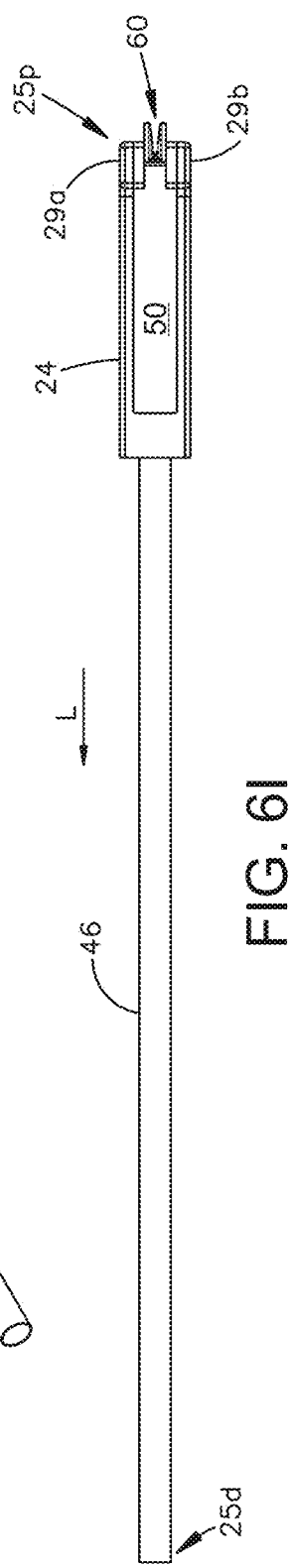

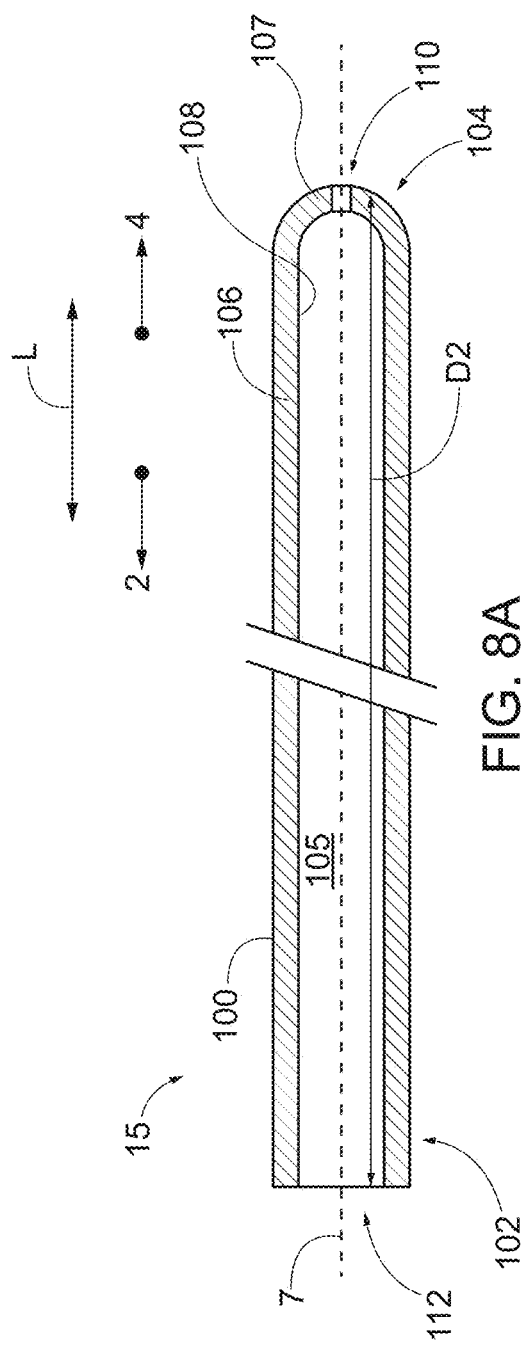
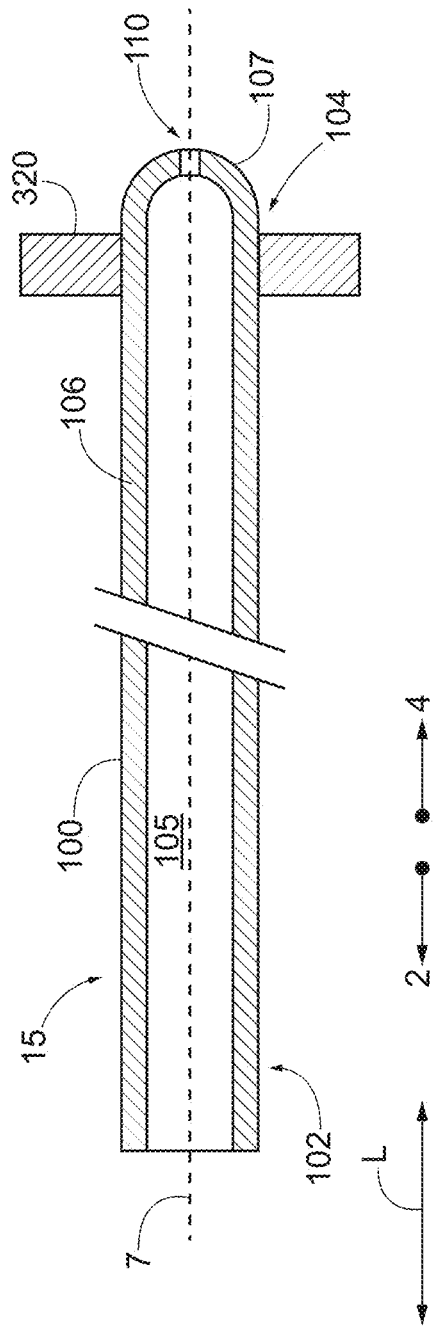

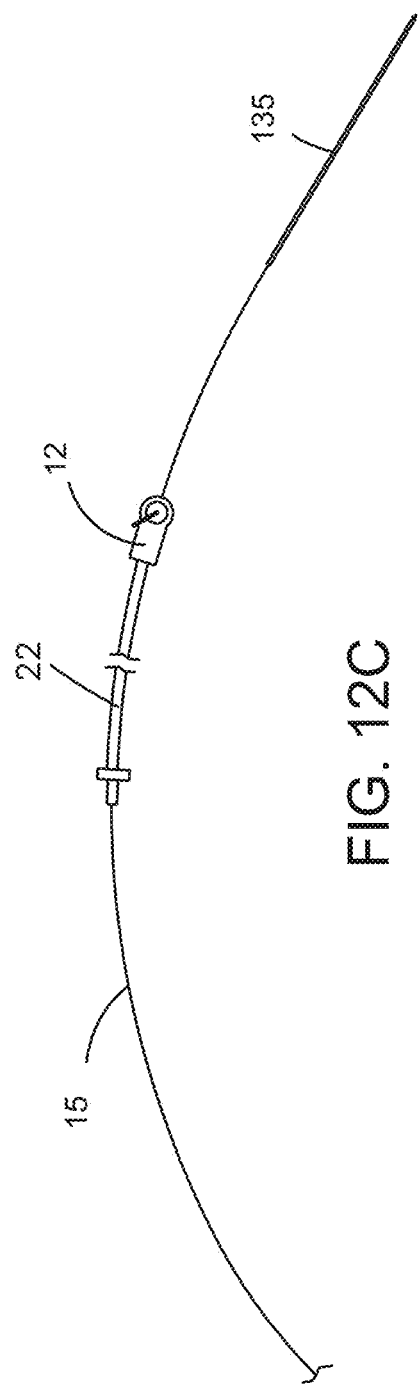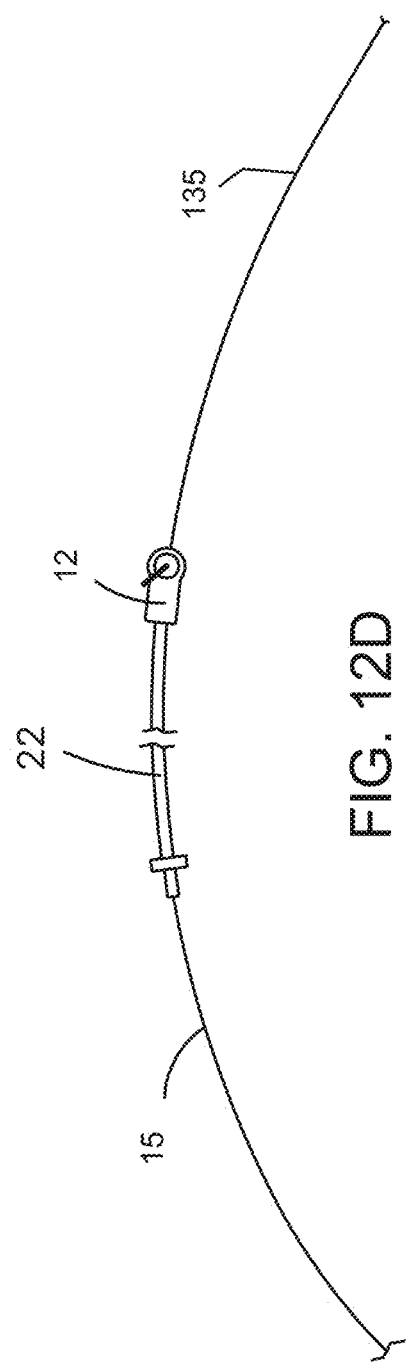

VASCULAR CLOSURE DEVICE WITH REMOVABLE GUIDE MEMBER

CROSS-REFERENCE TO RELATED APPLICATION

The present application is a divisional application of U.S. application Ser. No. 15/192,632, filed Jun. 24, 2016, now U.S. Pat. No. 10,555,727, which claims priority to and the benefit of U.S. Provisional Application Ser. No. 62/185,415, filed Jun. 26, 2015, the entire disclosures of which are incorporated herein by reference in their entireties.

TECHNICAL FIELD

The present disclosure relates to a vascular closure device with a removable guide member for a guide wire.

BACKGROUND

Percutaneous access of the vascular system for vascular device delivery is a common medical procedure. Typically this involves using a hollow needle to puncture a vessel, then introducing an introducer sheath to open the puncture site for the introduction of catheters and wire guides for navigation through the vascular system to facilitate delivery. For example, in many cases, vascular access requires introduction of catheters and guide wires through the femoral artery. Once the procedure is completed, the devices are removed from the patient and pressure is applied to the puncture site to stop the bleeding. Thereafter, the puncture may be sealed using a closure device. Closure devices generally consist of three basic sealing components: a toggle (or anchor) member, a sealing member (or plug), and a filament (or suture). To lock the components together within the puncture, a locking member may be used.

SUMMARY

An embodiment of the present disclosure is a vascular closure configured to be disposed along a guide wire toward a puncture of a vessel. The vascular closure device includes a sealing device configured to seal the puncture of the vessel, and a delivery assembly that releasably holds the sealing device. The vascular closure device includes a moveable guide member that is elongate along a longitudinal axis and that extends through at least a portion of the sealing device. The movable guide member includes a lumen that extends along the longitudinal axis and that is sized and configured to receive the guide wire as the vascular closure device is positioned along the guide wire. The guide member is moveable relative to the delivery assembly so as to be removed from the at least a portion of the sealing device.

Another embodiment of the present disclosure is a vascular closure configured to be disposed along a guide wire toward a puncture of a vessel. The vascular closure device includes a sealing device configured to seal the puncture of the vessel. The vascular closure device also includes a delivery assembly including a front end and a rear end spaced from the front end in a proximal direction, and the front end of the delivery assembly releasably holds the sealing device. A moveable guide member is supported by the delivery assembly and extends through at least a portion of the sealing device. The movable guide member includes a distal end, a proximal end spaced from the distal end in the proximal direction, and a lumen that extends from the distal end toward the proximal end in the proximal direction. The lumen is sized and configured to receive the guide wire through the distal end when the vascular closure device is disposed along the guide wire. The movable guide member is configured to translate relative to the delivery assembly from a first position where the movable guide member extends through the at least a portion of the sealing device, to a second position where the movable guide member does not extend through the at least a portion of the sealing device.

Another embodiment of present disclosure is a method for sealing a puncture of a vessel. The method comprising the step of positioning a guide member that extends through at least a portion of a sealing device along a guide wire such that a proximal end of a guide wire enters a lumen of the guide member. A delivery assembly supports the guide member and releasably holds the sealing device. The method includes the step of advancing the guide member and the sealing device along the guide wire in a distal direction. The method also includes moving the guide member relative to the delivery assembly along a proximal direction that is opposite to the distal direction so to as remove the guide member from the at least a portion of the sealing device.

BRIEF DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and systems shown. In the drawings:

FIG. 2 is a perspective view of the vascular closure device shown in FIG. 1, including a sealing device;

FIG. 3 is a partial cut-away view of the vascular closure device shown in FIG. 2;

FIG. 6E is a perspective view of the a release component, delivery component and a tensioning element of the vascular closure device shown in FIGS. 1-4;

FIG. 6F is a perspective cross-sectional view of the release component, delivery component, and the tensioning element shown in FIG. 6E, taken along line 6F-6F;

FIG. 6G is a perspective view of the delivery component and tensioning element of the vascular closure device shown in FIG. 6E;

FIGS. 6H and 6I are perspective and top views of the release component and tensioning element of the vascular closure device shown in FIGS. 1-4;

FIG. 8A is a sectional view of a guide member illustrated in FIG. 1;

FIG. 8B is a sectional view of a guide member including a gripping member, according to another embodiment of the present disclosure;

FIG. 1J is a schematic showing the deployment of the sealing device fully sealing the puncture site; and FIG. 12A-12D are schematic views illustrating removal of the guide member from the closure device.

DETAILED DESCRIPTION OF ILLUSTRATIVE EMBODIMENTS

Figure 1:
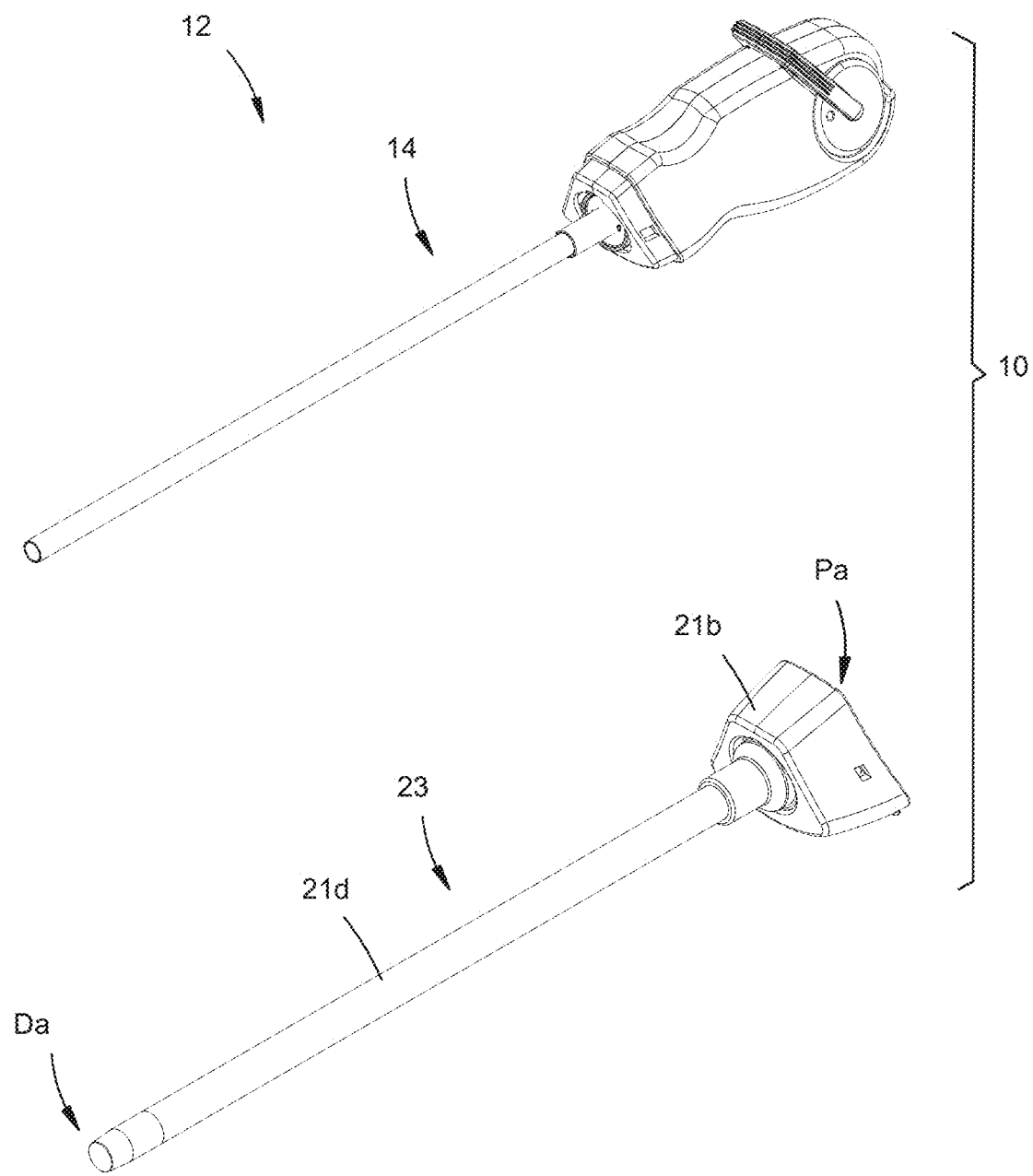
FIG. 1 is a perspective view of a vascular closure device of a puncture closure system in accordance with an embodiment of the present disclosure.

Certain terminology is used in the following description for convenience only and is not limiting. The words "right", "left", "lower" and "upper" designate directions in the drawings to which reference is made. The words "proximally" and "distally" refer to directions toward and away from, respectively, the individual operating the system. The terminology includes the above-listed words, derivatives thereof and words of similar import.

Referring to FIGS. 1-3, embodiments of the present disclosure include a puncture closure system 10 used to seal puncture in an arterial wall. The puncture closure system 10 includes an introducer (not shown), such as a dilator, and a vascular closure device 12 that is configured to seal the puncture in an arterial wall. The vascular closure device 12 includes an access sheath 23, a sealing device 18, and a delivery assembly 14 that releasably carries the sealing device 18 and that is insertable into the access sheath 23. The access sheath 23 can be inserted into the puncture along a guide wire 15 (FIG. 11A) and over the introducer (not shown) to form an insertion assembly. After the introducer is removed from the access sheath 23, the delivery assembly 14 can be inserted over the guide wire 15 into the access sheath 23 and coupled with the access sheath 23 to position the sealing device 18 (FIG. 11B) in the artery. As shown, the vascular closure device 12 includes a removable guide member 135 carried by the delivery assembly 14. The removable guide member 135 receives the guide wire 15 as further explained below.

Referring to FIGS. 1-3, the delivery assembly 14 can be inserted into and coupled to the access sheath 23. The access sheath 23 is elongate along a longitudinal direction L. The access sheath 23 defines a distal end DA, a proximal end PA, and an access channel 36 (FIG. 11A) that extends from the proximal end PA to the distal end DA along the longitudinal direction L. The access sheath 23 also includes a hub 21b and a shaft 21d that extends from the hub 21b. The proximal end, which can be referred to as the rearward end, of the access sheath includes the hub 21b that is configured to be coupled to a portion of the delivery assembly 14. In one example, the hub 21b includes a first engagement member (not shown) and the delivery assembly 14 includes a second engagement member (not shown) that couples the first engagement member so that the access sheath 23 and delivery assembly 14 are fixed with to each other. The first and second engagement members can be snap-fit features or other types of mechanical interlocks.

Figure 4:
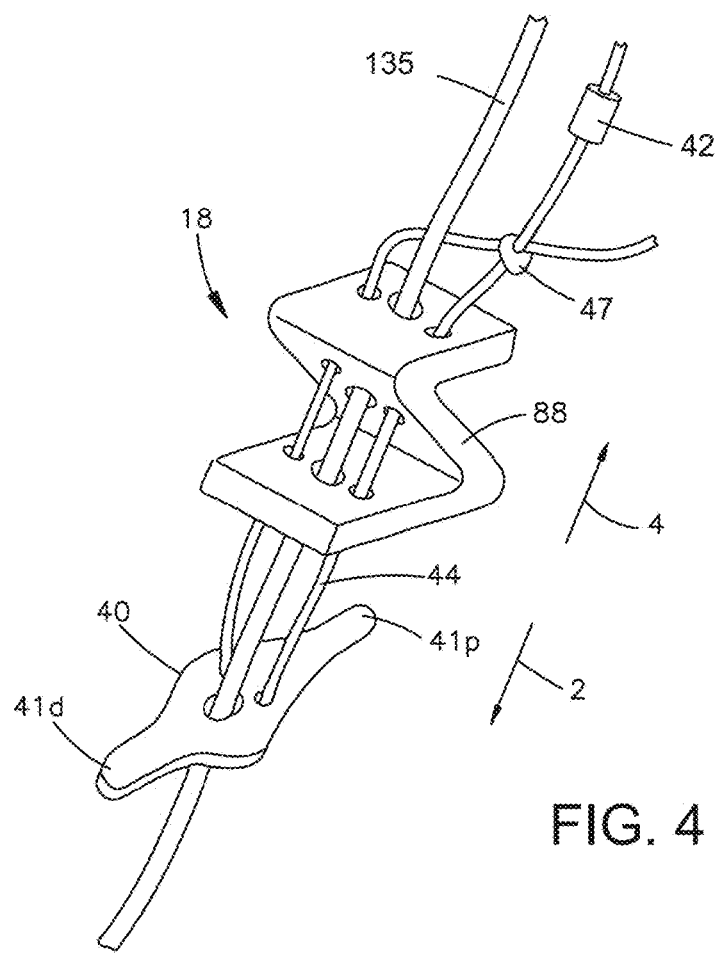
FIG. 4 is a perspective view of the sealing device in the vascular closure device illustrated in FIGS. 2 and 3.
Figure 5:
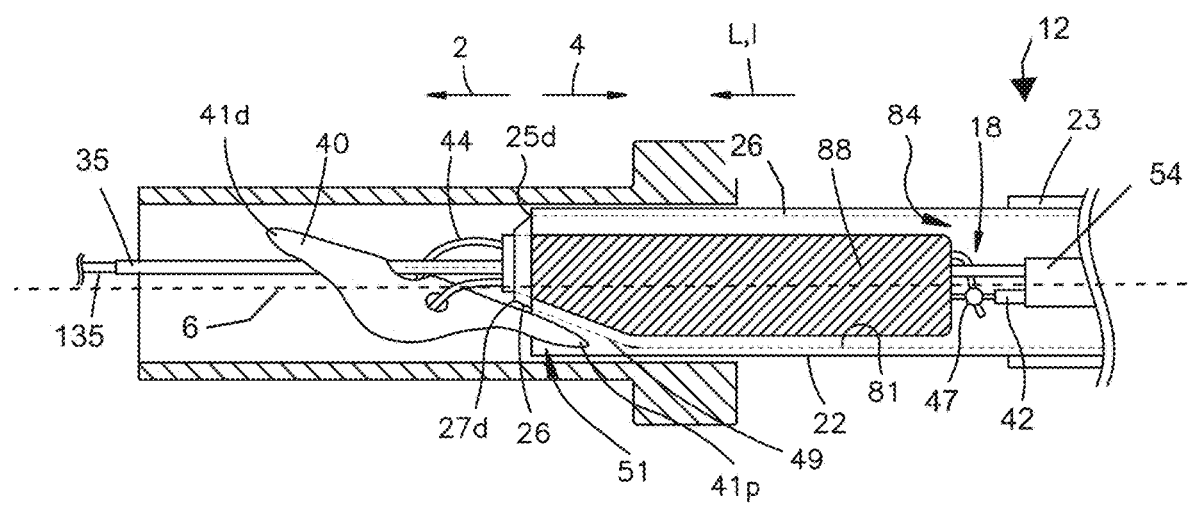
FIG. 5 is a detailed sectional view of a distal portion of the vascular closure device shown in FIGS. 1-4.

Turning to FIGS. 4 and 5, the vascular closure device 12 includes a sealing device 18 for sealing a puncture. The sealing device 18, which may be referred to as implantable unit, includes a toggle 40, a suture 44 coupled to the toggle 40, a plug 88 coupled to the suture 44 and spaced from the toggle 40 in a proximal direction 4, and a locking member 42 disposed on the suture 44 proximal to the plug 88. The vascular closure device 12 is configured such that after a distal portion of delivery assembly 14 is inserted through the puncture site of the vessel, the sealing device 18 can be deployed to seal or otherwise close the puncture site. The delivery assembly 14 controls orientation of the toggle 40 as the sealing device 18 is advanced through the access sheath 23 in an easier and more efficient manner. Furthermore, the delivery assembly 14 is also configured to reduce forces required to deploy the sealing device 18 and seal the puncture. In one example, deployment forces are reduced by providing a guide member 135 that 1) guides the delivery assembly 14 into position, and 2) can be removed from the sealing device 18 and/or completely from the delivery assembly 14. Removal of the guide member 135 prior to deployment of the sealing device 18 creates additional space within the vascular closure device 12, which in turn, helps reduces forces required to fully deploy the sealing device 18.

Referring to FIGS. 4 and 5, the toggle 40 includes a distal end 41d, a proximal end 41p opposite to the proximal end 41p, and a plurality of apertures (not numbered) extending therethrough. The suture 44 is extends through the apertures as illustrated such that an end of the suture 44 is formed into a slidable knot 37. The knot 37 is slidable along the suture 44 between the plug 88 and the locking member 42. In an implanted state, the toggle 40 is adjacent an inner surface of the vessel and the locking member 42 squeezes the toggle 40 the plug 88 against the vessel to seal the puncture.

The sealing device 18 is formed with materials suitable for surgical procedures. The toggle 40 can be made of any biocompatible material. For example, the toggle 40 can be made of a polylactic-coglycolic acid or other synthetic absorbable polymer that degrades in the presence of water into naturally occurring metabolites. In other embodiments, the toggle 40 can be made of stainless steel, biocorrodible iron, and biocorrodible magnesium. It should be appreciated, however, that the toggle 40 can be made of other materials and can have other configurations so long as it can be seated inside the vessel against the vessel wall. The plug 88 can comprise a strip of compressible, resorbable, collagen foam and can be made of a fibrous collagen mix of insoluble and soluble collagen that is cross linked for strength. It should be appreciated, however, that the plug member 88 can have any configuration as desired and can be made from any material as desired. The suture 44 can be any elongate member, such as, for example a filament, thread, or braid.

Referring to FIGS. 2 and 3, the delivery assembly 14 includes a handle member 20, a release component 22, a delivery component 26, a tensioning element 28 coupled to the delivery component 26, one or more actuators 38 operatively to the release component 22, a tamper 54 disposed along the suture 44, and a guide member 135. The toggle 40 is trapped between the release component 22 and the delivery component 26 as shown in FIG. 5. When the delivery assembly 14 is fully seated in the access sheath 23 as shown in FIGS. 2 and 3, the shaft 21d of the access sheath 23 extends along the release component 22 and the delivery component 26 in a distal direction 2. The release component 22 is also operatively associated with the suture 44 such that actuation of the actuator 38 1) releases the toggle 40, and 2) applies tension to the suture 44. The tension applied the suture 44 by the actuator 38 urges the toggle 40 against the delivery component 26 and orients the toggle 40 into the sealing position. The delivery assembly 14 also carries the removable guide member 135 such that the guide member 135 extends through the sealing device 18 and is configured to receive a guide wire 15. As shown, the guide member 135 extends through the plug 88 and toggle 40. In another example, the delivery assembly 14 can be configured so that the guide member 135 (and guide wire 15) extends through the plug 88 but along the side of the toggle 40. The guide member 135 is configured to be removed from at least the sealing device 18 before the sealing device 18 is deployed to seal the puncture. Each component of the vascular closure device 12 will be described next.

Referring again FIGS. 2 and 3, the delivery assembly 14 is elongate along a longitudinal direction L and includes a rear end 16p and a front end 16d spaced from the rear end 16p along an axis 6 that is aligned with the longitudinal direction L. The delivery assembly 14 defines a length D1 that extend from the front end 16d to the rear end 16p along the longitudinal direction L. The longitudinal direction L can include and define a distal direction 2 that extends from the rear end 16p toward the front end 16d. Further, the longitudinal direction L can include and define a proximal direction 4 that is opposite the distal direction 2 and that extends from front end 16d toward the rear end 16p. The delivery assembly 14 is configured to insert the toggle 40 into the vessel along an insertion direction I through the access sheath 23. The longitudinal direction L can be aligned with the insertion direction I during a portion of the sealing procedure.

Referring to FIGS. 2 and 3, in accordance with the illustrated embodiment, the delivery assembly 14 includes a handle member 20. The handle member 20 includes a housing 21a and a cavity 21c defined at least partly by housing 21a and a hub 21b of the access sheath 23. The cavity 21c is sized to contain a portion of the release component 22, the delivery component 26, and the tensioning element 28. As shown, the handle member 20 supports the release component 22 such that release component 22 extends from handle member 20 in the distal direction 2. The delivery component 26 also supported by the handle member 20 and extends along the distal direction 2 within a lumen of the release component 22. A portion of delivery component 26 is shown in dashed lines in FIGS. 2 and 3. The tensioning element 28 is contained in the housing 21a and is coupled to a proximal end of the release component 22. The actuator 38 is coupled to both the handle member 20 and the release component 22.

Turning to FIGS. 6H and 6I, the release component 22 is elongate along a first or longitudinal direction L defines a distal end 25d and a proximal end 25p spaced from the distal end 25d along the longitudinal direction L. In accordance with the illustrated embodiment, the release component 22 includes a hub 24 and a release tube 46 that is fixed to the hub 24 and that extends from the hub 24 in the distal direction 2. The hub 24 is disposed at the proximal end 25p of the release component 22. As illustrated, the release hub 24 includes a pair of tabs 29a, 29b, and a pulley 60 coupled to and disposed between the tabs 29a, 29b. The pulley 60 defines a curved track that receives the suture 44 as will be explained below. The hub 24 defines a slot 50 that is elongate along the longitudinal direction L and is aligned with the release tube 46. The slot 50 is sized to receiver a coupler 31 of the tensioning element 28.

Referring to FIGS. 6H and 6I, the release tube 46 includes a release tube body 51 that is elongate along the longitudinal direction L. The release tube body 51 defines a release tube channel 52 (FIG. 6D) that extends from the hub 24 toward the distal end 25d. In the illustrated embodiment, the release tube channel 52 extends completely through the release tube body 51 from the hub 24 to the distal end 25d. The release tube body 51 is cylindrical such that the release tube channel 52 is radially enclosed. It should be appreciated, however, that the release tube channel 52 can extend partially through the release tube body 51 as desired and that the release tube body 51 can have other configurations as desired. For example, the release tube body 51 can be U-shaped such that the release tube channel 52 is partially radially open. As shown, the release tube channel 52 is sized to slidably receive a portion of the delivery component 26 such that the release component 22 is movable relative to the delivery component 26. As shown in FIG. 6D, the suture 44 extends around the pulley 60 along the guide track and into the tensioning element 28. As shown, the tensioning element 28 is positioned alongside the release component 22. It should be appreciated, however, that in some embodiments, the tensioning element 28 is positioned proximal to the release tube and is in-line with the release component 22 such that the suture 44 extends through the release tube 46 and into the tensioning element 28 along the first direction L.

Figure 6A:
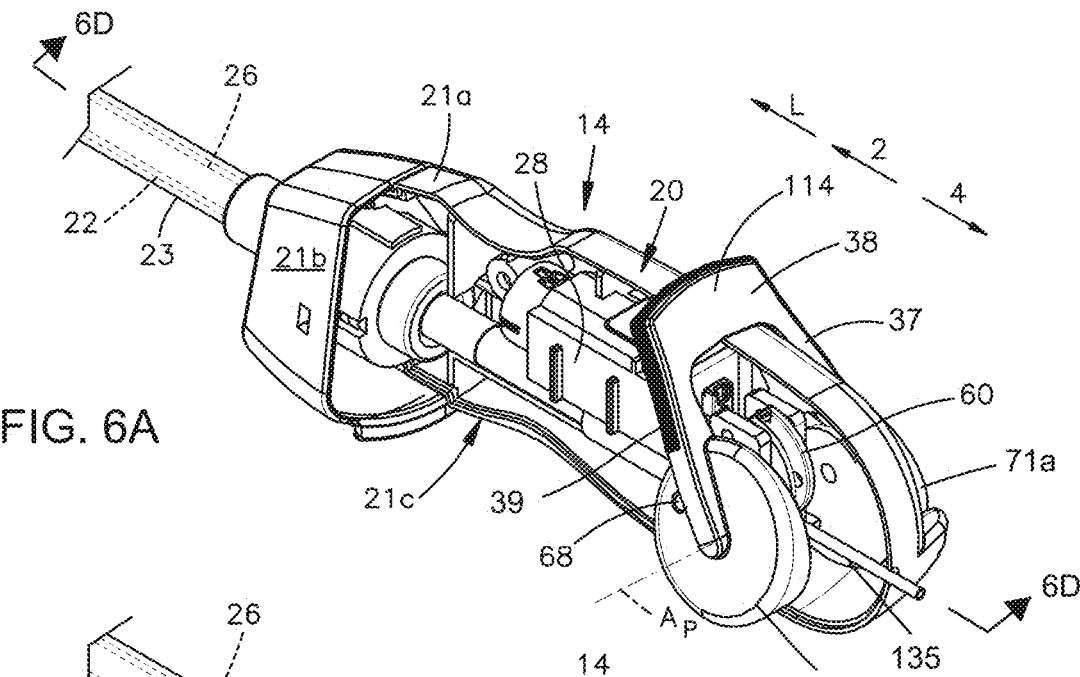
FIGS. 6A-6C are rear perspective views of the vascular closure device with portions of the device removed for clarity.
Figure 6B:
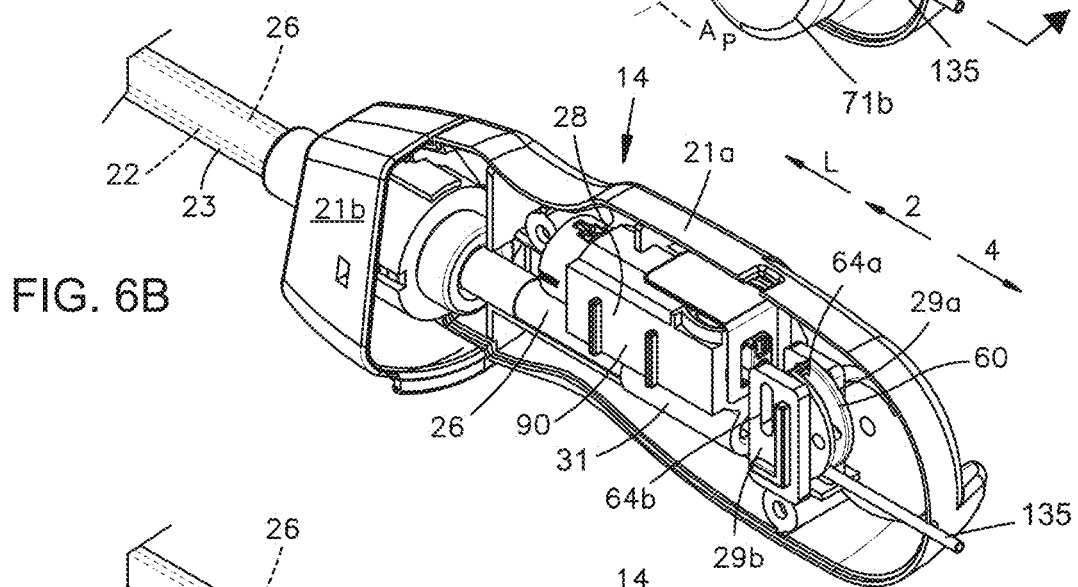
Figure 6C:
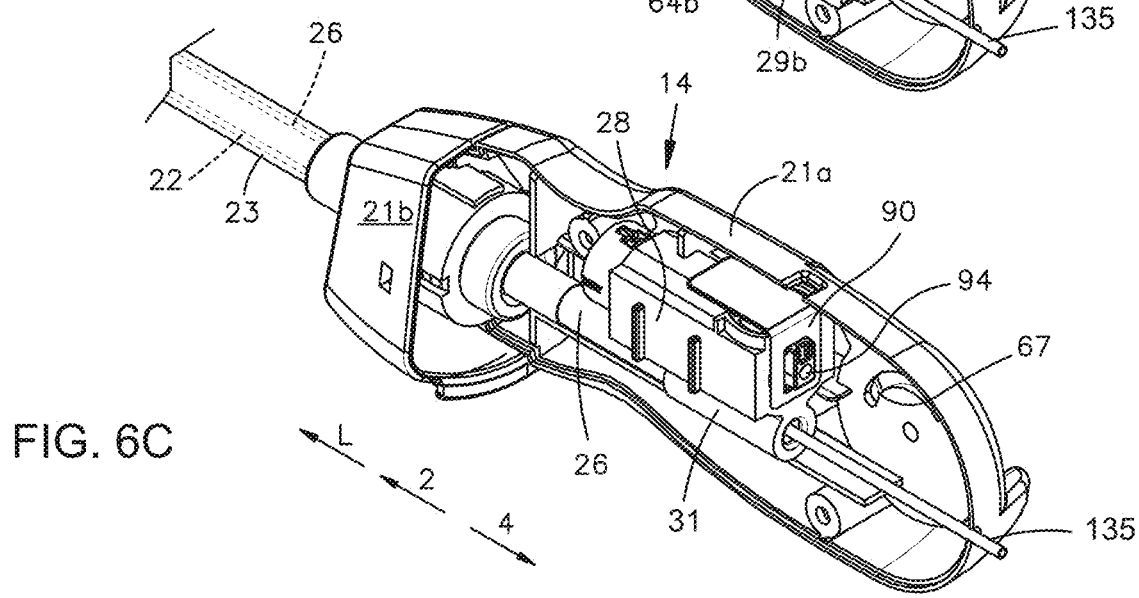
Figure 6D:
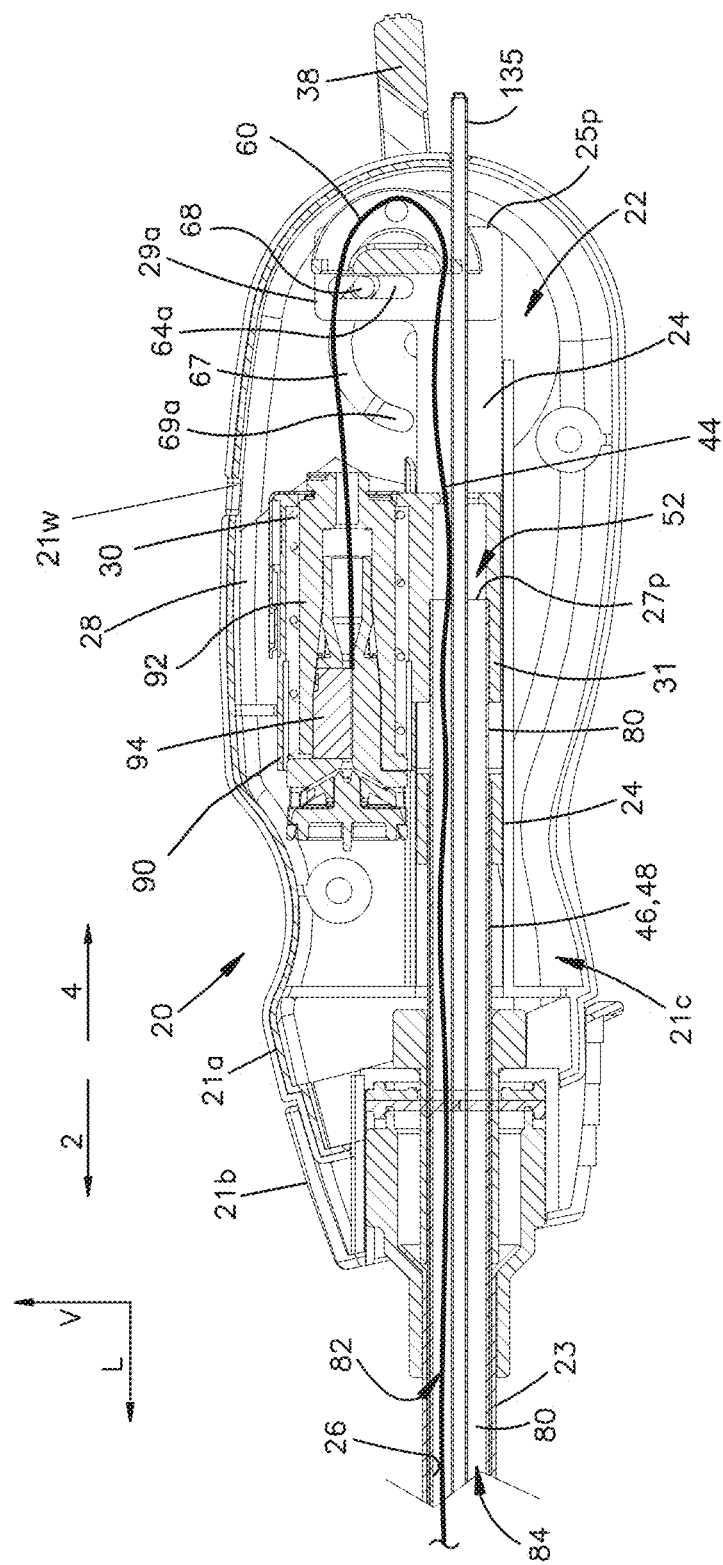
FIG. 6D is a cross-sectional view of the vascular closure device shown in FIG. 6A, taken along line 6D-6D.

Referring to FIGS. 6A-6D, and 6H, 6I, the release component 22 can be operatively coupled to the actuator 38 via one or more mating members. As best shown in FIGS. 6A and 6H, the release component 22 includes at least one mating member 64 that mates with a corresponding mating member 68 of the actuator 38. The mating member 64 is shown as a pair of matting member 64a,64b that are engaged with mating member 68 so as to transfer the motion of the actuator 38 to the release component 22. In the illustrated embodiment in FIGS. 6A and 6I, the release component mating member 64 is a pair of slots 64a and 64b defined by the respective pair of tabs 29a and 29b of the hub 24. Each slot 64a and 64b is elongate along a vertical direction V that is perpendicular to the longitudinal direction L. The mating member 68, which can be a pin, is disposed inside the slots 64a and 64b such that actuation of the actuator 38 causes the release component 22 to translate along the longitudinal direction L. It should be appreciated, however, that the mating member 64 can have any configuration as desired. For example, the mating member 64 can be a bore having a diameter that is equal to that of the pin such that translation of the actuator 38 causes the release component 22 to translate along the first direction L.

FIGS. 6D-6G illustrates a delivery component 26 designed to carry the sealing device 18. As illustrated, the delivery component 26 extends along the inside of the release component 22 toward the front end 16d of the delivery assembly 14. The delivery component 26 includes a delivery tube body 80 that is elongate along the direction L. The delivery tube body 80 defines a distal end 27d, a proximal end 27p spaced from the distal end 27d in the direction L, and an inner surface 81. The inner surface 8 defines a delivery tube channel 84 that extends at least partially through the delivery tube body 80 along the direction L. The delivery tube channel 84 extends completely through the delivery tube body 80 from the proximal end 2'7p to the distal end 27d. However, the channel 84 can extend along a portion of the delivery tube body 80. In the illustrated embodiment, the delivery tube body 80 is cylindrical such that the delivery tube channel 84 is radially enclosed. It should be appreciated, however, that the delivery tube channel 84 can extend partially through the delivery tube body 80. The delivery tube body 80 can have other configurations as desired. For example, the delivery tube body 80 can be U-shaped such that the delivery tube channel 84 is partially radially open. The distal end 27d of delivery component holds at least a portion of the sealing device 18 (FIG. 5). In accordance with the illustrated embodiment, the proximal end 2'7p of delivery component is fixed to the tensioning element 28. Because the tensioning element 28 is fixed to the housing 21a, the delivery component 26 is fixed to the housing 21a and thus the handle member 20.

Referring to FIG. 5, the delivery assembly 14 releasably carries at least a portion of the sealing device 18. In particular, the plug 88 and locking member 42 are retained within the delivery tube channel 84, while the toggle 40 is configured to be initially trapped between the delivery component 26 and the release component 22. The tamper 54 is also positioned in the channel 84. As shown, the distal end 27d of the delivery component 26 defines an offset surface 49, which can be angled with respect to the longitudinal axis 6. The offset surface 49 and inner surface 81 of the release tube body 51 define a cavity 51 that receives the proximal end 41p of the toggle 40 when the release component 22 is in the initial position. The angle of the offset surface 49 can define the orientation of the toggle 40 in this initial position. In the initial position, the distal end 41d of the toggle 40 is spaced some distance in the distal direction 2 beyond the distal ends 25d and 27d of the release component 22 and delivery component 26, respectively. The suture 44 extends from the toggle 40 through the delivery tube channel 84, the tamper 54, through the proximal end 2'7p and around the pulley 60 along the guide track. The suture 44 is coupled to the tensioning element 28 (FIG. 6D). The guide member 135 extends through the channel 84 and exits the front end 16d of the vascular closure device 12.

The release component 22 and delivery components 26 are described above has having tubular shaped bodies. It should be appreciated that the release and delivery components can have other configurations. For instance, the release component can be elongate rod, or an elongate rod with a tubular ring coupled to its distal end. The delivery component can be configured such that only a portion thereof has a tubular shape.

Figure 7A:
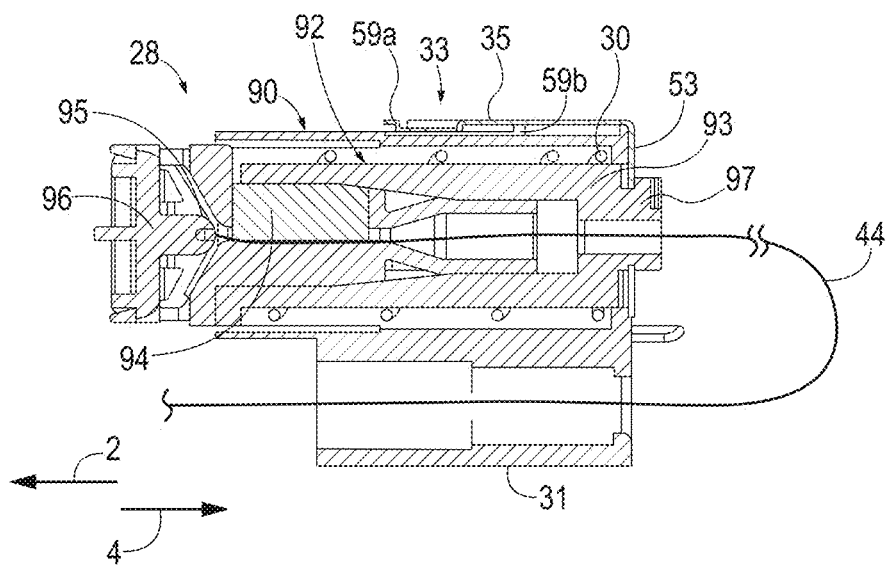
FIGS. 7A and 7B are side sectional views illustrating operation of the tensioning element illustrated in FIG. 6D.
Figure 7B:
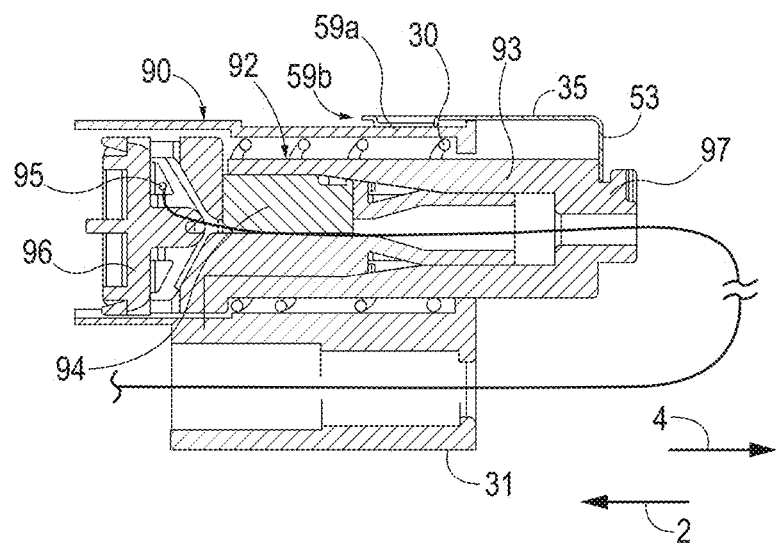

As shown in FIGS. 6D-6G, 7A and 7B, the vascular closure device 12 includes a tensioning element 28. In accordance with the illustrated embodiment, the tensioning element 28 includes a tensioner housing 90, a moveable cartridge assembly 92 disposed with the tensioner housing 90, a drag member 94 in the moveable cartridge assembly 92, and a spring 30 positioned between the tensioner housing 90 and the cartridge assembly 92. The suture 44 extends from the release component 22 (FIG. 6D) around the pulley 60 and into the tensioner housing 90 and through the drag member 94, and is coiled within a tensioning element 28, e.g. at cartridge assembly 92. A terminal end of the suture 44 is attached to the cartridge assembly 92. At rest, the spring 30 biases the cartridge assembly 92 in a distal direction 2, as shown in FIG. 7A. Application of tension the suture 44 moves the cartridge assembly 92 in the proximal direction 4 into from the first position into the second position, as shown in FIG. 7B.

The tensioner housing 90 is coupled to the delivery component 26 and the handle member 20. As shown in FIG. 6B, the tensioner housing 90 includes a coupler 31 that is attached to the delivery component 26. The coupler 31 as illustrated is a tubular component that receives the proximal end 2'7p of the delivery tube body 80. The tensioner housing 90 is fixed the housing 21a of the handle member 20. As illustrated, the delivery tube body 80 is fixed to the coupler 31, which is fixed to the tension housing 90. This, in turn, indirectly fixes the delivery component 26 to the housing 21a. Thus, the tension housing 90 and the delivery component 26 are fixed to the housing 21a.

As best shown in FIGS. 7A and 7B, the movable cartridge assembly 92 includes a cartridge housing 93 with a cavity (not numbered), a drag member 94 within the cavity, a spool 95 adjacent the drag member 94 and an end cap 96. The end cap 96 secures the spool 95 to the cartridge housing 93 and the drag member 94. The spool 95 includes a coiled section of suture 44. The cartridge housing 93 includes a nose 97.

The drag member 94 and is attached to the cartridge assembly 92 such that a frictional force is applied to the suture 44 by the drag member 94. In the illustrated embodiment, the drag member 94 is a silicon member that pinches the suture 44. The tensioning element housing 90 and drag member 94 are similar to that described in U.S. Patent Application Publication No. 2013/0178895, which is incorporated by reference herein. It should be appreciated, however, that the drag member 94 can have other configurations as desired.

As shown in FIGS. 6E, 6F, 7A and 7B, the tensioning element 28 also includes a feedback device 33 that can provide a tactile, auditory and/or visual feedback when the appropriate tension is applied to the suture 44. As shown, the feedback device 33 is configured as a plate 35. The plate 35 includes a transverse section 53 coupled to the nose 97 of the cartridge housing 93, and a plurality of different colored sections 58a, 58b, and 58c. The different sections 58a-58c of the plate 35 align with a window 21w (FIG. 6D) depending on the position of the tensioner housing 90 during the deployment procedure. In one example, section 58a is red, section 58b is yellow, and section 58c is green. The plate 35 also includes projection 59a that rides over a ridge 59b of the tensioner housing 90 and produces an audible sound when the feedback device 33 is advanced in a proximal direction 4 over the ridge 59b, as explained below.

In use, the tensioning element 28 can control tension applied to suture during release and deployment of the sealing device 18. The frictional force applied to the suture 44 by the drag member 94 can be high enough to maintain the suture 44 in tension after the actuator 38 has been actuated and the toggle 40 has been urged against the distal end 27d of the delivery component 26. When the delivery assembly 14 and access sheath 23 are pulled in the proximal direction 4 relative to the toggle 40, the frictional force applied to the suture 44 by the drag member 94 can be low enough to allow the suture 44 to dispense from the spool 95 in the tension element 28. When all of the suture 44 has dispensed from the spool 95, continued pulling force applied to the delivery assembly 14 in the proximal direction 4 causes the cartridge assembly 92 to move in the proximal direction 4 in the cartridge housing 93 to compress the spring 30. The spring 30 functions as a counter to the pulling force applied to the delivery assembly 14.

As shown in FIGS. 7A and 7B, tension is applied to the suture 44 (through pulling the delivery assembly 14 proximally), the cartridge assembly 92 moves relative to the tensioner housing 90 from a first position, as shown in FIG. 7A, into a second or tensioned position, as shown in FIG. 7B. As the tension along the suture 44 increases and the cartridge assembly 92 moves, the plate sections 58a, 58b and 58c sequentially align with the window 21w. For example, at a first level of tension, plate section 58c is aligned with the window 21w, at a second level of tension, plate section 58b is aligned with the window 21w, at a third or predetermined threshold level of tension, plate section 58a is aligned with the window 21w. Thus, alignment of different colored sections with window 21w provides a visual indication of the level of tension applied to the suture. As illustrated, when the cartridge assembly is in the first position as shown FIG. 7A, the plate section 58c is aligned with the window 21w. When the cartridge assembly is in the tensioned position as shown FIG. 7B, the plate section 58a is aligned with the window 21w, providing a visual indication that a predetermined tension limit along the suture 44 has been met.

Accordingly, when predetermined deployment tension is applied to the suture 44, such as when the toggle 40 is adjacent the inner surface of the arterial wall, the cartridge assembly 92 moves into the tensioned position (FIG. 7B) so that: 1) the colored section 58a is aligned with the housing window 21w providing a visual indication of the applied tension; and/or 2) the plate 35 flexes as the projection 59a rides over the ridge 59b and retracts back against the housing 90 causing an audible click. It should be appreciated that other mechanisms for providing tactile, auditory, and/or visual feedback can be used.

Turning to FIGS. 6A-6D, the delivery assembly 14 includes one or more actuators 38 that release sealing device 18. As illustrated, the delivery assembly 14 includes one actuator 38. The actuator 38 is operable to cause the release component 22 to move in the proximal direction 4 from a first or initial position relative to the delivery component 26 into a second or releasing position relative to the delivery component 26. The actuator 38 can also apply a tensile force to the suture 44 during, or subsequent to, movement of the release component 22 from the initial position into the releasing position. The description herein refers to the release component 22 being moveable relative to the delivery component 26. But the delivery assembly 14 can be configured so that the delivery component 26 is moveable relative to the release component 22. When the actuator 38 is actuated, the release component 22 moves in the proximal direction 4 thereby releasing the proximal end 41p of the toggle 40 from between the release component 22 and the delivery component 26. As the release component 22 moves in the proximal direction 4, the suture 44 will be pulled in the proximal direction 4 to thereby place the suture 44 in tension and urge the toggle 40 against the distal end 27d of the delivery component 26. At this point, the toggle 40 is oriented in the sealing position (see FIG. 11D). In the sealing position, the toggle 40 has been repositioned so that the toggle 40 is placed against the distal end 27d of the delivery component 26 and is oriented more transversely with respect to the axis 6 compared to the position when the toggle 40 is restrained by the release component 22.

In accordance with the embodiment as shown in FIGS. 6A-6D, the actuator 38 can be configured as a lever that is rotatably coupled to the handle member 20. Rotation of the lever can cause the release component 22 to translate relative to the delivery component 26 as to release the toggle 40. The actuator 38 can include a pair of side members 71a and 71b rotatably coupled to each side of the housing 21a, a first leg 37a that extends from one of the side members 71a, a second leg 37b that extends from the other side member 71b, and a transverse member 39 that connects the first leg 37a to the second leg 37b. The actuator 38 is configured to pivot about a pivot axis $A_P$ that is perpendicular to the axis 6. The pivot axis $A_P$ may or may not intersect axis 6. The housing 21a defines a curved housing slot 67 that is curved with respect to the pivot axis $A_P$. The curved housing slot 67 has a first end 69a (FIG. 6D) and second end (not numbered) spaced apart from the first end along the proximal direction 4. The mating member 68 of the actuator 38 can be a pin 68 that is coupled to and extends between the side members 71 and 71b at a location that is offset from the pivot axis $A_P$. The pin 68 extends through curved housing slot 67 and through the elongate slots 64a and 64a of the hub 24 of the release component 22 to couple the actuator 38 to the release component 22. As the actuator 38 pivots about the pivot axis $A_P$, the pin 68 moves from the first end 69a the curved housing slot 67 toward the second end of the curved housing slot 67, and also moves along the slots 64a and 64b along the vertical direction V. Because the release component 22 is moveable relative to housing 21a, as pin 68 moves along the curved housing slot 67, the pin 68 advances the hub 24 of the release component 22 in the proximal direction 4. The result, in accordance with the illustrated embodiment, is that rotation of the actuator 38 causes the release component 22 to translate in the longitudinal direction L. Translation of the release component 22 releases the toggle 40, as further explained below. It should be appreciated, however, that the actuator 38 can have other configurations as desired and is not limited to the disclosed lever.

Operation of the actuator 38 causes the release component 22 to release the toggle 40 from delivery assembly 14. As shown, rotation of the actuator 38 moves the release component 22 in the proximal direction 4 relative to the delivery component 26 into a releasing position (not illustrated) thereby releasing the proximal end 41p of the toggle 40 from between the release component 22 and the delivery component 26. As the release component 22 moves in the proximal direction 4, the suture 44 is pulled in the proximal direction 4 to thereby place the suture 44 in tension. Application of tension along the suture 44 urges the toggle 40 against the distal end 27d of the delivery component 26 and orients the toggle 40 into the sealing position. Accordingly, the release component 22 is configured to restrain the toggle 40 of the sealing device 18 during insertion of the vascular closure device 12 into the vessel and subsequently release the toggle 40 so that the toggle 40 can be oriented for the sealing procedure. In the illustrated embodiment, the actuator 38 and release component 22 are configured such that continuous movement of the actuator 38 relative to the housing 21a will move the release component 22 in the proximal direction 4, thereby releasing the toggle 40 from the release component 22 and subsequently applying tension to the suture 44. The actuator 38 may have different configurations compared to that described above and illustrated in the figures. For example, in an alternative embodiment, actuation of the actuator cause tension to be applied to the suture 44 as the toggle 40 is being released. In still other alternative embodiments, the delivery assembly 14 can include a first actuator to release the toggle 40 and a second actuator that tensions the suture 44.

As described above, the vascular closure device also includes a tamper 54. The tamper 54 is at least partially disposed within the delivery assembly 14. The tamper 54 is disposed along the suture 44 relative to the locking member 42 in the proximal direction 4. The tamper 54 includes a first lumen (not numbered) that receives the suture 44 therethrough and a second lumen (not numbered) that receives the guide member 135 therethrough. After the requisite tension is applied to the suture 44, the tamper 54 can be advanced along the suture 44 in the distal direction 2 to tamp the locking member 42 against the plug 88. The tamper 5 can be used to tamp the locking member 42 into a compressed plug 88 in order to seal the puncture.

Figure 9A:
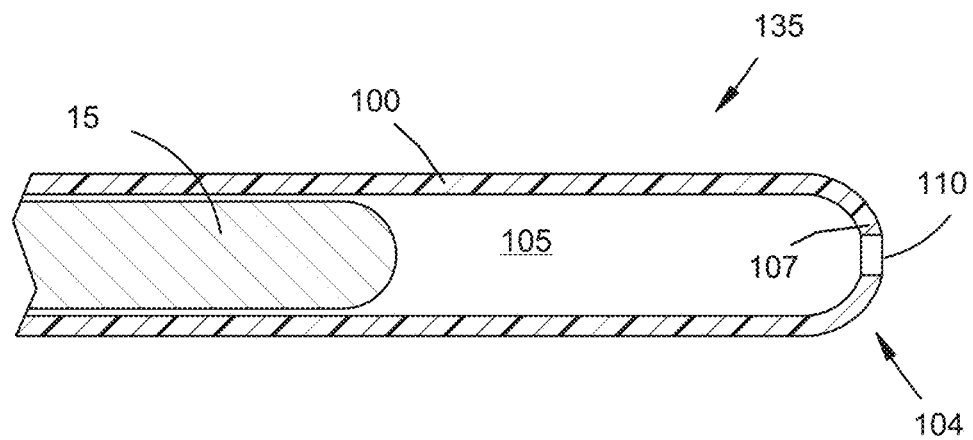
FIG. 9A is a sectional view of a proximal end of the guide member shown in FIG. 8A.

In FIGS. 8A and 9A, the vascular closure device 12 includes a moveable guide member 135 that receives the guide wire 15. The moveable guide member 135 includes a tubular guide body 100 defining a distal end 102, a closed proximal end 104 spaced from the distal end 102 along a central axis 7, and a lumen 105 extends from the distal end 102 toward the closed proximal end 104. The moveable guide member 135 defines a length D2 (also referred to as a second length D2) that extends from the distal end 102 to the proximal end 104 along the central axis 7. The distal end 102 defines an opening 112 that receives a proximal most end of the guide wire 15. The body 100 includes a side wall 106 and proximal wall 107 that extends at least partially along a direction that is perpendicular to the longitudinal direction L. The guide member 135 includes at least one aperture 110 located along the proximal wall 107. However, as explained below, the aperture need not be positioned on the proximal wall 107. The aperture can be placed along the side wall 106 (See FIGS. 8B, and 8B-9D). The aperture 110 can have a circular, oval, or elongated shape as needed. Furthermore, one aperture or a plurality of apertures could be used.

Automatic removal of the guide member 135 can be accomplished using the closed proximal end 104 and is illustrated in FIGS. 12A-12D and described further below. As this is accomplished in the setting of vascular closure and blood and other liquids are present within the setting, the guide wire and/or guide member 135 may become wetted with blood or saline during handling. For this reason it may be advantageous to position an aperture 110 at or proximate the closed proximal end 104 of the guide member 135 as illustrated in FIGS. 8A and 9A. During advancement with wetted components, the guide wire 15 may trap air within the guide member 135. With the aperture 110 placed at a proximal position along the guide member 135 will permit entrapped liquids or air to vent out of the lumen 105. For instance, with the aperture 110, air that might be pushed ahead of the incoming guide wire 15 is vented from the guide member 135 proximally.

As shown in FIGS. 8A and 9A, one way to accomplish automatic removal of the guide member 135 is close down the proximal end 104 of the guide member 135, which prevents the guide wire from sliding out the proximal end of the guide member 135. Thus, as the vascular closure device 12 is advanced over the guide wire 15, the guide wire 15 enters the distal opening 112 of the guide member 135, travels through the length of the lumen 105, and then encounters the closed proximal end 104. Further advancement of either the guide wire 15, or vascular closure device 12 over the guide wire, will push the guide member 135 in a proximal direction 4 out of the sealing device and the delivery assembly 14 as needed.

FIG. 8B illustrates another embodiment of the moveable guide member. FIG. 8B illustrates a moveable guide member 335 that is also configured to receive the guide wire 15. The moveable guide member 335 is similar to the moveable guide member 135 shown in FIG. 8A. Accordingly, the same reference numbers are used to identify features that are common to the moveable guide member 135 and the moveable guide member 335. In accordance with the alternative embodiment, the guide member 335 is configured for manual removal from the delivery assembly 14. As shown, the moveable guide member 335 includes a gripping member 320 positioned at the proximal end 104. A user can grab the gripping member 320 and pull the guide member 335 in the proximal direction 4 to remove the moveable guide member 335 from the sealing device 18 and, as needed, the entire delivery assembly 14.

Figure 9B:
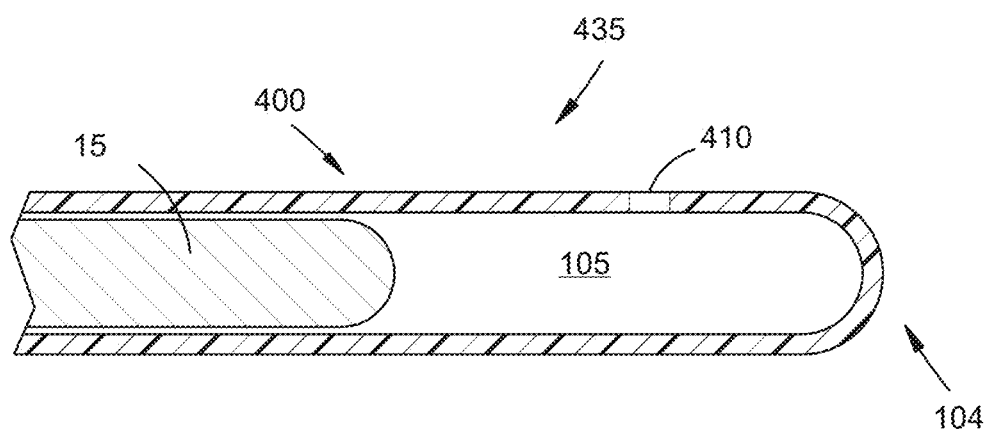
FIG. 9B is a sectional view of a proximal end of the guide member according another embodiment of the present disclosure.

FIG. 9B shows an alternate embodiment of the moveable guide member that can include apertures disposed along its side. FIG. 9B illustrates a moveable guide member 435 that is also configured to receive the guide wire 15. The moveable guide member 435 is similar to the moveable guide member 135 shown in FIG. 8A. Accordingly, the same reference numbers are used to identify features that are common the moveable guide member 135 and the moveable guide member 435. In accordance with the alternative embodiment, the moveable guide member 435 includes side apertures 410 near the proximal end 104.

Figure 9C:
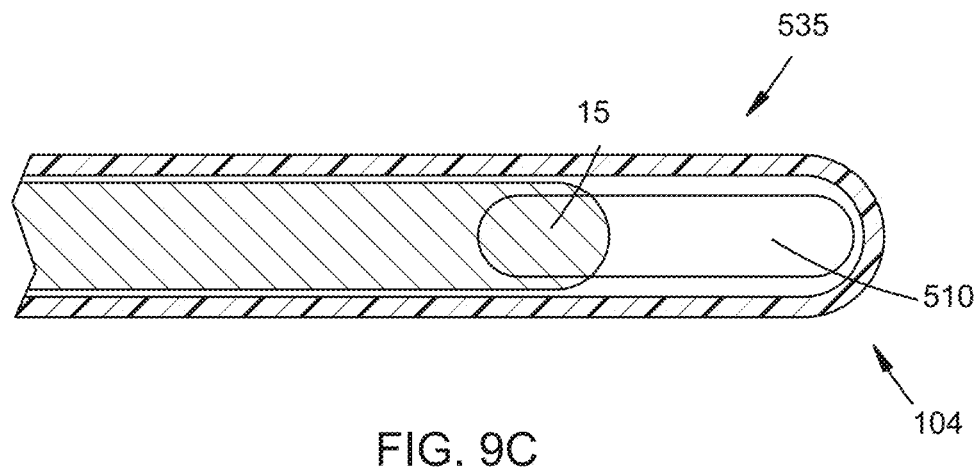
FIG. 9C is a sectional view of a proximal end of the guide member according another embodiment of the present disclosure.

FIG. 9C illustrates a moveable guide member 535 that is also configured to receive the guide wire 15. The moveable guide member 535 is similar to the moveable guide member 135 shown in FIG. 8A. Accordingly, the same reference numbers are used to identify features that are common the moveable guide member 135 and the moveable guide member 535. In accordance with the alternative embodiment, the moveable guide member 535 includes an elongate slot 510 disposed along the side wall 106. The slot 510 is shown disposed near the proximal end 104. The slot 510 has particular utility, in that it also has the advantage of the guide wire 15 becoming visible to the user as it reaches the closed proximal end 104 of the guide member 535. Thus, the guide member 535 provides a visual indication of guide wire position within the guide member 535.

Figure 9D:
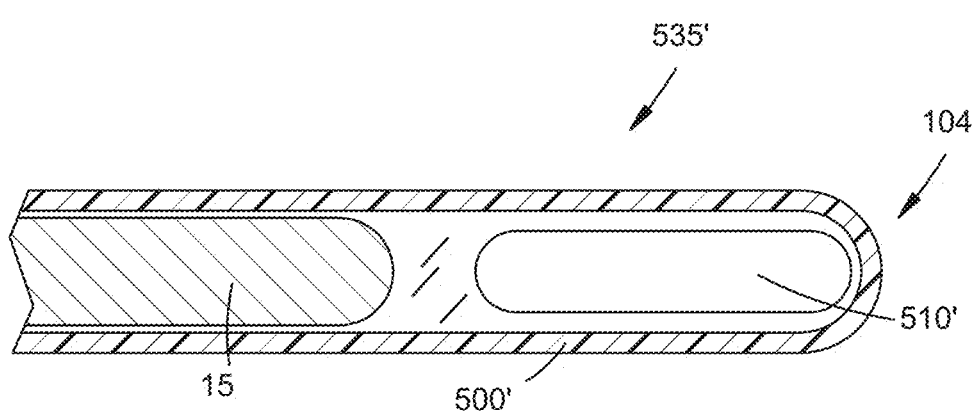
FIG. 9D is a sectional view of a proximal end of the guide member according another embodiment of the present disclosure.

FIG. 9D illustrates another moveable guide member 535' that is also configured to receive the guide wire 15 and that also permits visualization of the guide wire 15. The moveable guide member 535' is similar to the moveable guide member 535 shown in FIG. 9B and moveable guide member 135 shown in FIG. 8A. Accordingly, the same reference numbers are used to identify features that are common the moveable guide member 135, 535 and the moveable guide member 535'. In accordance with the alternative embodiment, the moveable guide member 535' includes a body 500' formed from a clear material, and an elongate slot 510' disposed along the side wall 106. Moveable guide member 535' enhances visualization of the guide wire by forming the guide member body 500' with a clear material. It should be readily apparent that any other embodiment of the guide member described herein can be manufactured with a clear material.

Figure 10:
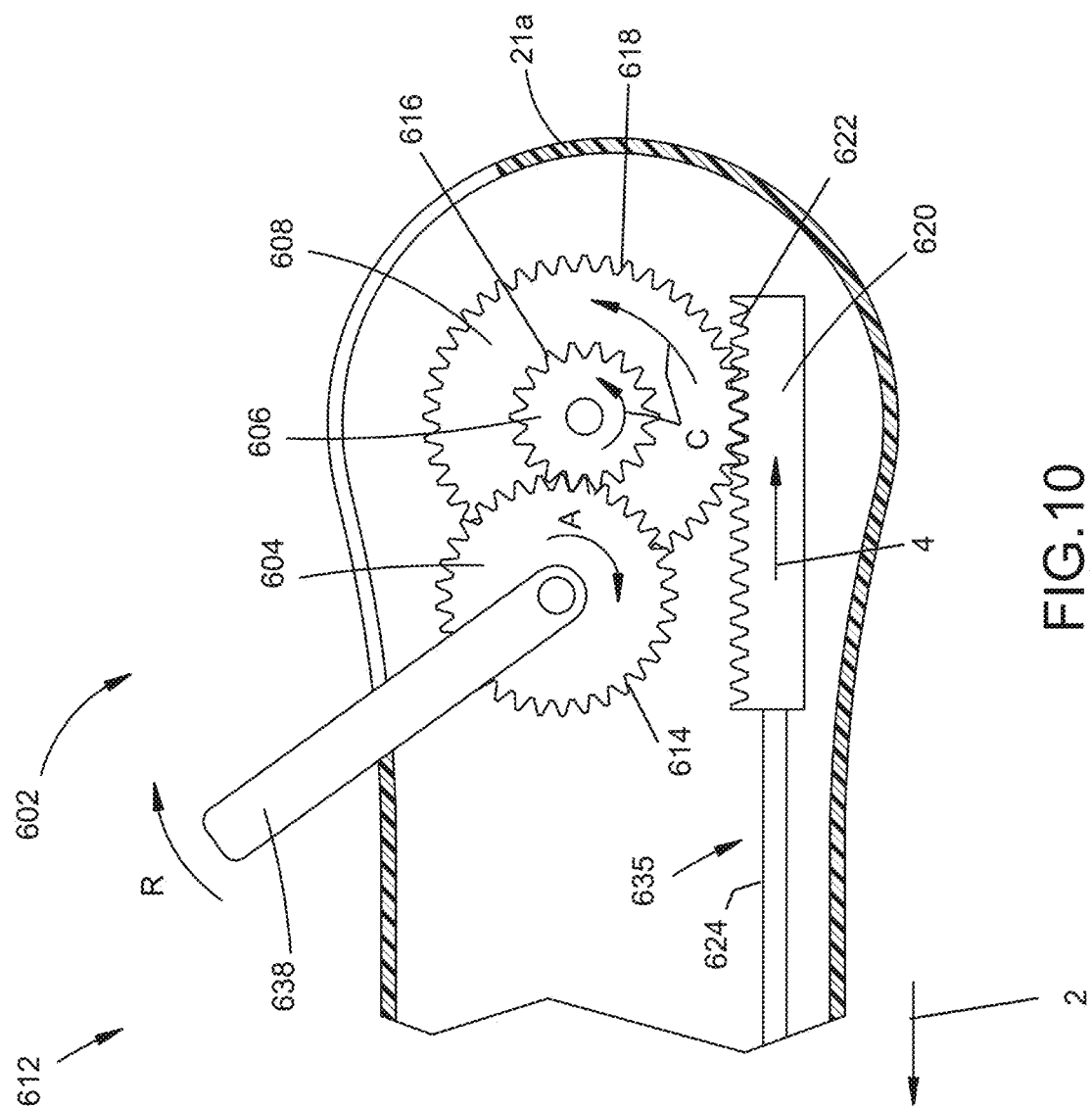
FIG. 10 is sectional view of illustrating an actuator configured to move the guide member relative to the sealing device, according to an embodiment of the present disclosure.

FIG. 10 illustrates another embodiment of the vascular closure device 612 configured to automatically remove a moveable guide member 635 from the sealing device 18 (not shown). The vascular closure device 612 is similar to the vascular closure device 12 described above. For ease of illustrations, the same reference numbers identify features that are common to vascular closure device 12 and the vascular closure device 612. As illustrated, the vascular closure device 612 includes a moveable guide member 635 coupled to an actuator 602.

As shown in FIG. 10, the moveable guide member 635 includes an engagement end 620, configured as a gear rack, and a shaft 624 that extends from the gear rack 620 in the distal direction 2. The gear rack 620 defines a set of teeth 622. The guide member 635 includes a lumen that receives the guide wire 15.

Still referring to FIG. 10, the actuator 602 is configured to advance the guide member 635 in a proximal direction 4 so as remove the guide member 635 from the sealing device 18 (not shown). The actuator 602 could be located at the handle housing 21a as illustrated. The actuator 602 includes a lever 638 and multiple gears 604, 606 and 608. Gear 608 is coupled to an engagement to the gear rack 620. The first gear 604 includes a first set of teeth 614. The second gear 606 includes a second set of teeth 616 that mesh with the first set of teeth 614. The third gear 606 includes a third set of teeth 618 that mesh with the teeth 622 of the gear rack 620. External to handle housing 21a is lever 638 coupled to a first gear 604. The third gear 608 is rotationally coupled to the second gear 606 so as to rotate along with rotation of the second gear 606.

Operation of actuator 602 causes the guide member 635 to move out of the sealing device 18. Actuation of lever 638 in the direction of the arrow R shown will rotate gear 604 in a clockwise direction R, thus rotating gear 606 and gear 606 in a counter-clockwise direction C. Gear 608 is engaged with the gear rack 620, which is slideable within the housing 21a along a proximal direction 4. Counter-clockwise movement of gear 608 then moves rack 620 in a proximal direction 4, which when connected to guide member 635, also slides guide member 635 in the proximal direction 4 within the housing 21a.

Continuing with FIG. 10, the arrangement and sizing of gears as shown will amplify the movement of the guide member 635 over the movement of the lever 638. This could be adjusted as needed for whatever stroke of the guide member 635 is required. It should be noted that in the present configuration of the vascular closure device 12, the plug 88 is approximately 1.0 inches in length, which taken together with the position of the toggle, and the length of the guide member 635 needed to extend from the toggle as shown in FIG. 1, the expected required stroke of the guide member 635 would be up to about 2.0 inches. This distance should be easily accommodated with gear arrangement shown in FIG. 10. In alternative embodiments, the stroke can be greater than 2.0 inches as needed. While a gear based actuator is illustrated, other types of actuators can be used to advance the guide member 635 in a proximal direction 4. For instance, the actuator 602 can be a screw-type actuator, slideable, or spring biased. In other embodiments, the actuator 602 may also cause toggle release as described above. In such an embodiment, the actuator may include a first phase that removes the guide member 635 from at least the sealing device, and a second phase that deploys the sealing device as discussed above.

Embodiments of the present technology will now be described with respect to exemplary large bore procedures that utilize the vascular closure device 12. In order to perform any of the related procedures, the user gains percutaneous access to, for example, the femoral artery, causing a puncture site in the artery. To gain percutaneous access to the artery, the Seldinger technique may be used. For example, a hollow bore needle is inserted into the artery. A guide wire 15 is then advanced through the hollow needle and into the femoral artery a sufficient distance to allow removal of the needle without the guide wire 15 pulling out of the vessel. Removing the needle leaves the guide wire 15 in place, with a portion of the guide wire 15 extending into the artery. The guide wire 15, extending from outside the patient into the femoral artery, provides for an entry guide for other medical devices including the vascular closure device 12. Therefore, once the guide wire 15 is positioned in the vessel of the patient, catheters, or introducers, of gradually increasing diameters are advanced over the guide wire and through the puncture into the artery to further open the puncture site. Then, an introducer/procedure access sheath set (i.e. an introducer inside an access tube or sheath) is moved along the guide wire 15 such that a distal end of the sheath moves into the vessel through the puncture site. And once positioned, the introducer can be removed such that the sheath provides for sizable access to the vessel interior from outside the body.

After the relevant procedure is completed in the artery, the puncture site is closed or sealed. The vascular closure system 10 as describe above and illustrated may be used to seal the puncture site. FIGS. 11A-11I show schematic views of the vascular closure system 10 during the process of closing a puncture site 200 in a vessel (e.g. artery) wall 204.

Figure 11A:
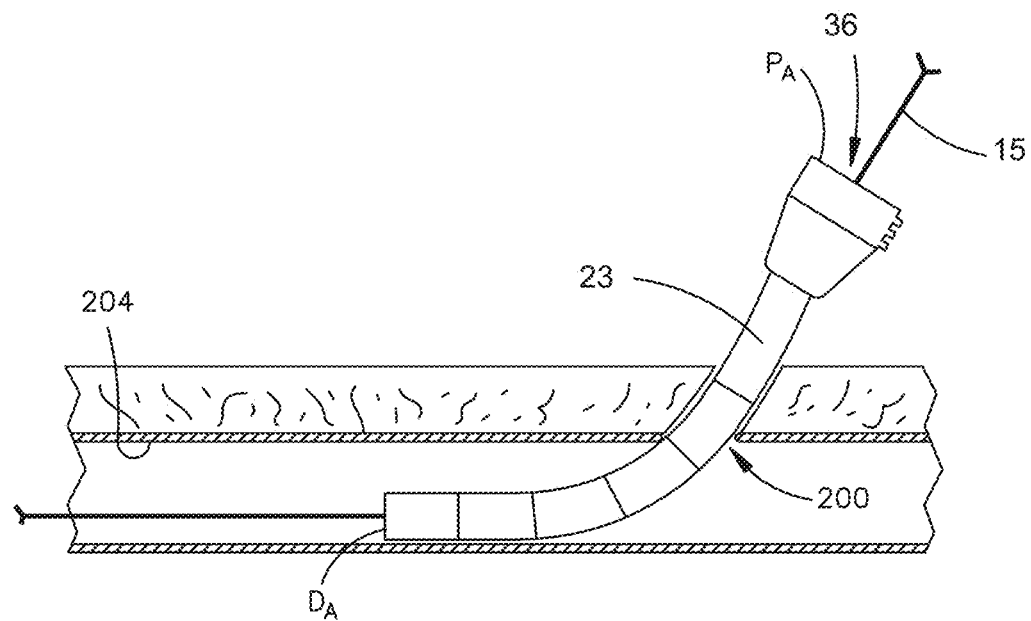
FIG. 11A is a schematic showing an access sheath partially disposed within a vessel through a puncture site in the vessel.

Now in reference to FIG. 11A, to deliver the vascular closure device 12 to the puncture site 200 so that the sealing device 18 can seal the puncture site 200, the introducer/procedure sheath set is replaced with a closure access sheath 23. For example, as shown in FIG. 11A, the procedure sheath is exchanged for the closure access sheath 23 by removing the procedure sheath from the patient, leaving the guide wire 15 in place, and subsequently moving the closure access sheath 23 along the guide wire 15 or otherwise positioning the access sheath 23, such that a portion of the access sheath 23 is disposed within the vessel through the puncture site 200. As shown in FIG. 11A, the access sheath 23 is configured to couple to the delivery assembly 14 when the delivery assembly 14 is inserted into the access channel 36 along the insertion direction I.

Figure 11B:
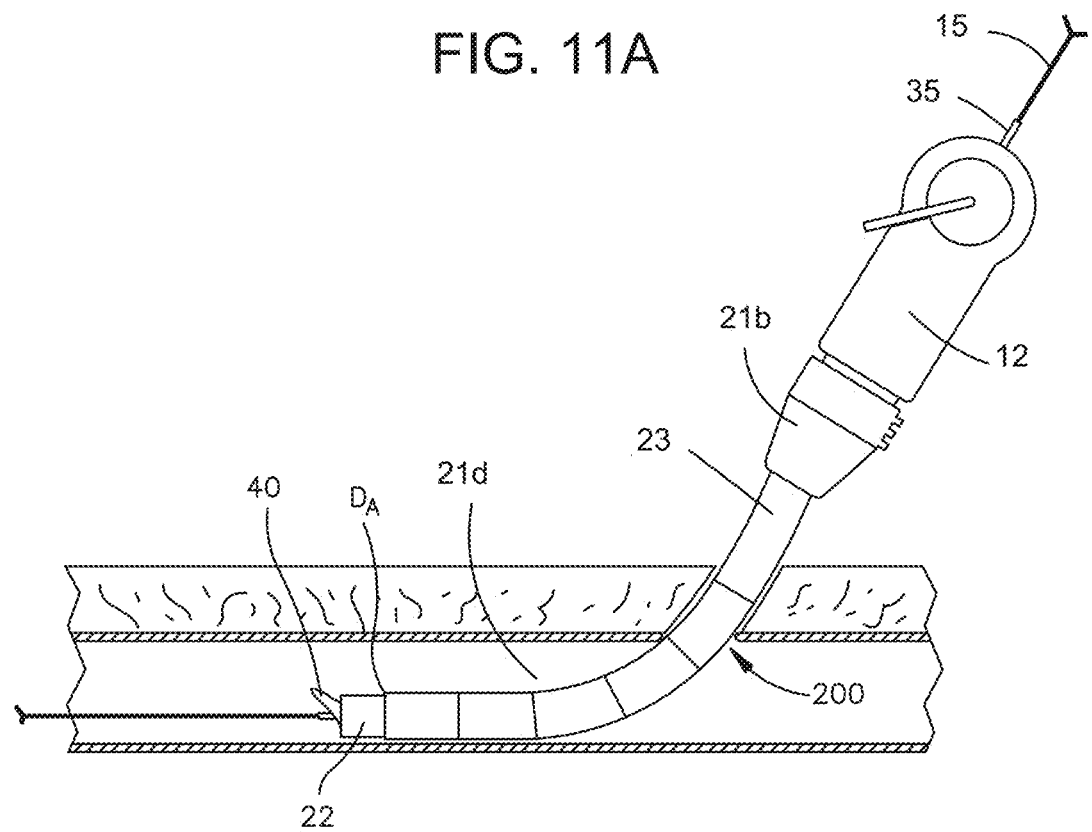
FIG. 11B is a schematic showing the closure device of FIG. 1 translated into an access channel of the access sheath such that a distal end of the toggle is positioned distal to a distal end of the access sheath.
Figure 11C:
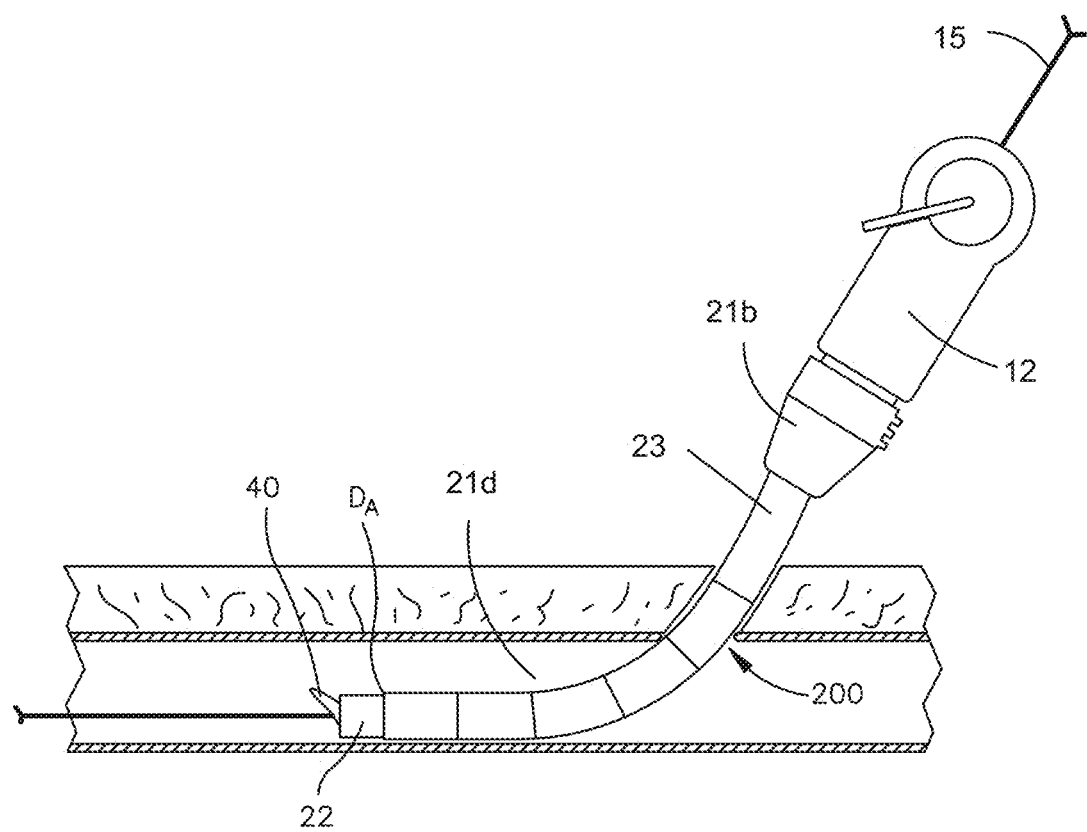
FIG. 11C is a schematic showing the guide member 135 removed from the closure device.

As shown in FIG. 11B, the vascular closure device 12 can be positioned by translating the vascular closure device 12 into the access channel 36 along the insertion direction I such that the toggle 40 protrudes from the distal end DA of the access sheath 23 and into the vessel. Once fully inserted, the delivery assembly 14 can couple to the sheath hub 21b. As shown in FIG. 11B, a proximal end 41p the toggle 40 is trapped between the release component 22 and the delivery component 26 while the vascular closure device 12 is being moved into the vessel through the puncture site 200 of the vessel. While the proximal end 41p of the toggle 40 is trapped, the toggle 40 is oriented in a pre-sealing position whereby at least the proximal end of the toggle 40 is prevented from dragging against the vessel wall during positioning of the toggle 40 within the vessel. At this point, the guide member 135, having fulfilled the function of allowing passage of a guide wire 15 through the vascular closure device 12, may be removed from the device as shown in FIG. 11C. This reduces the compression on the plug 88 by creating more space within the vascular closure device, and removes a high friction surface, allowing the plug 88 to fold more easily in subsequent deployment steps.

Figure 11D:
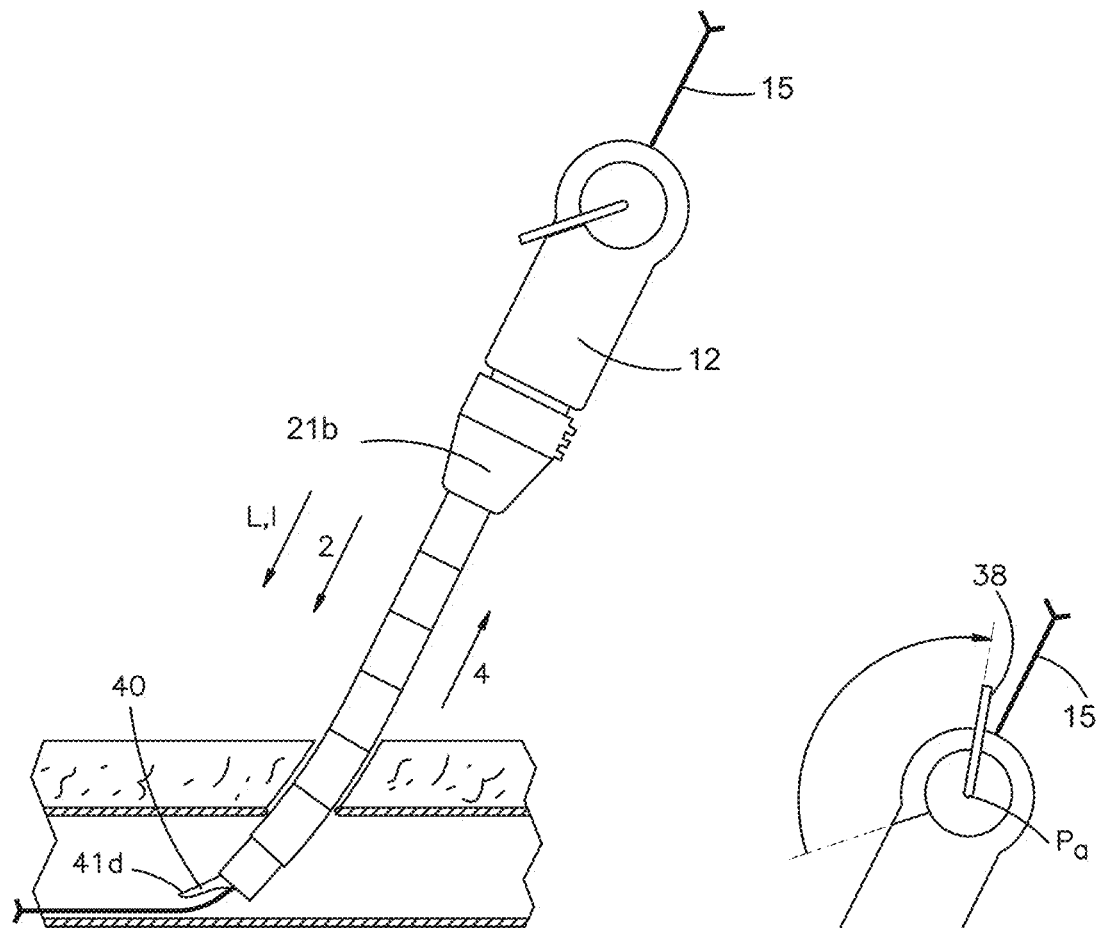
FIG. 11D is a schematic showing the access sheath and closure device combination pulled in a proximal direction such that the toggle is proximate to the puncture site.
Figure 11E:
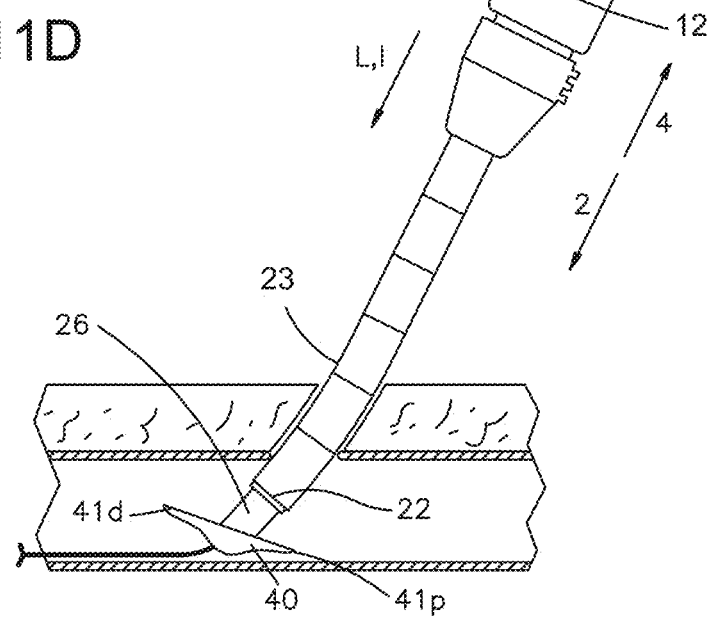
FIG. 11E is a schematic showing actuation of the actuator to release the toggle and apply a tension to a filament.

Once the vascular closure device 12 is properly positioned within the access sheath 23, the toggle 40 (e.g. the entire access sheath 23 and vascular closure device 12 combination) can be pulled in a proximal direction such that the toggle 40 is adjacent the puncture site 200. While the toggle 40 is being positioned adjacent the puncture site 200 the toggle 40 is in the pre-sealing position (or an insertion position) as shown in FIG. 11D. And once the toggle 40 is in pre-sealing position, the actuator 38 is actuated to a) to transition the toggle 40 into a released position where the toggle 40 is released from the release tube, and b) subsequently apply a tension to the suture 44 so as to pull the toggle 40 against the distal end of the delivery component 26 as shown in FIG. 11E. At this point the toggle 40 will be oriented in a sealing or transverse position as shown in FIG. 11E.

Figure 11F:
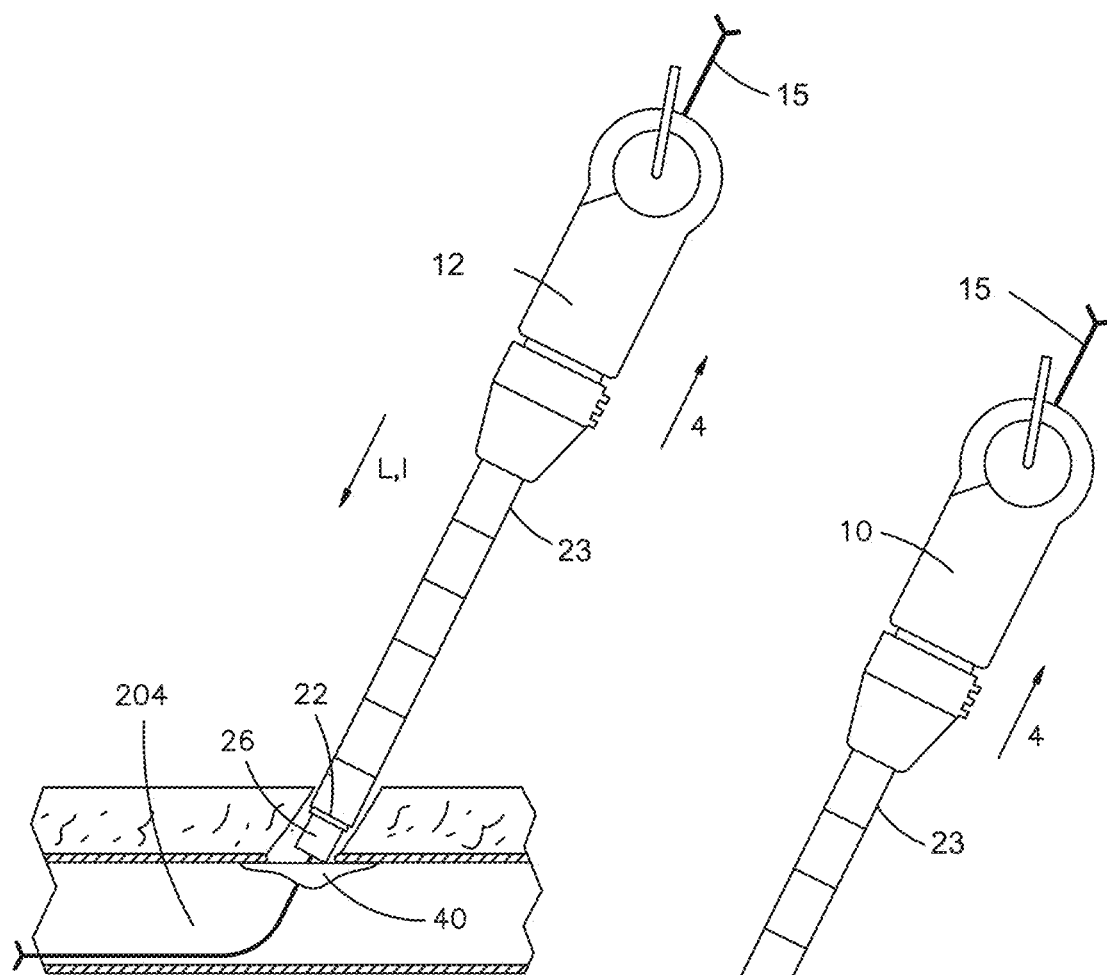
FIG. 11F is a schematic showing the deployment device being pulled in a proximal direction such that the toggle abuts the vessel wall.
Figure 11G:
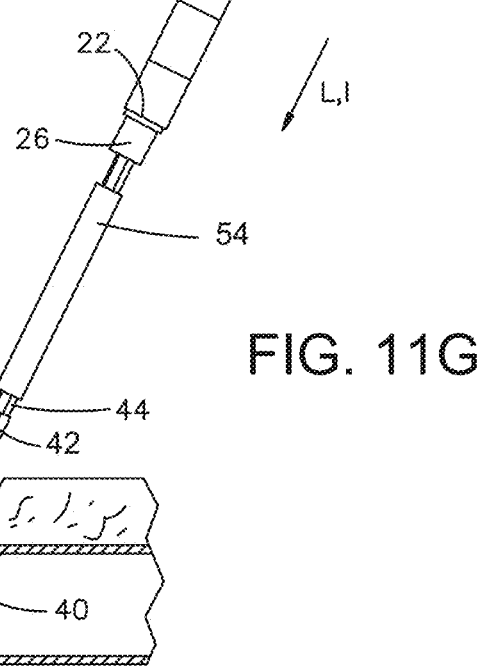
FIG. 11G is a schematic showing deployment of a plug of the closure device.
Figure 11H:
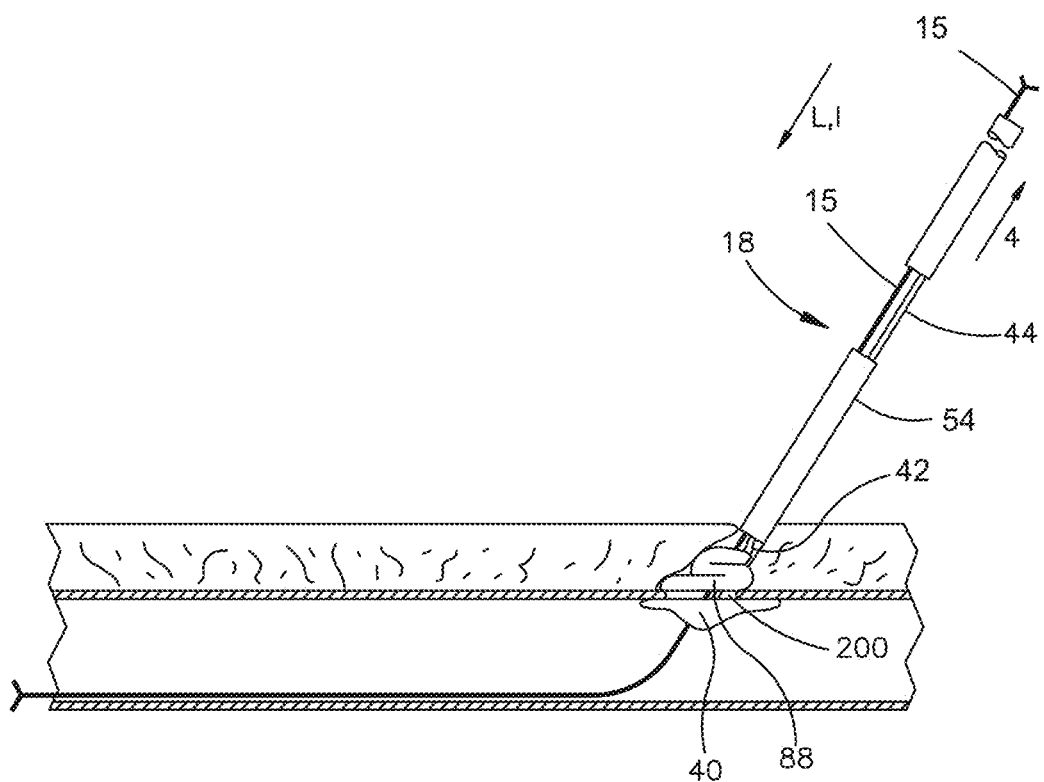
FIG. 11H is a schematic showing deployment of the a locking member against the plug.

With the toggle 40 in the sealing position as shown in FIG. 11E, the delivery assembly 14 along with the access sheath 23 can together be pulled in a proximal direction 4 such that the toggle 40 abuts the vessel wall 204, as shown in FIG. 11F. As shown in FIG. 11G, further pulling of the delivery assembly 14 and sheath 23 in the proximal direction 4 applies tension to the suture 44 and will cause the sealing device 18, including the toggle 40, plug 88, a locking member 42, and tamper 54 to be withdrawn from the delivery component 26. In other words, pulling the delivery assembly 14 in the proximal direction transitions the sealing device 18 from an engaged configuration into a deployed configuration. In the engaged configuration, the toggle 40 abuts the distal end of the delivery tube. In addition, the plug 88, locking member 42, and tamper 54 are inside the delivery tube. In the deployed configuration, the toggle 40 is withdrawn from the distal end of the delivery tube and the at least one of the plug 88, locking member 42, and tamper 54 are removed from the within the delivery tube. By pulling on the suture 44 in a direction away from the vessel (i.e. in a direction opposite the insertion direction I) the suture 44 is tensioned and the toggle 40 is moved fully into position against an inner surface of the vessel wall at the puncture site 200, as shown FIG. 11G. The tension in the suture 44 also pulls the plug 88 into the puncture site 200, and causes the plug 88 to substantially fill the puncture site 200 as shown in FIG. 12H. After the plug 88 is in contact with blood or other fluids within the puncture site 200, the plug 88 will expand and fill the remainder of the puncture site 200.

Figure 11I:
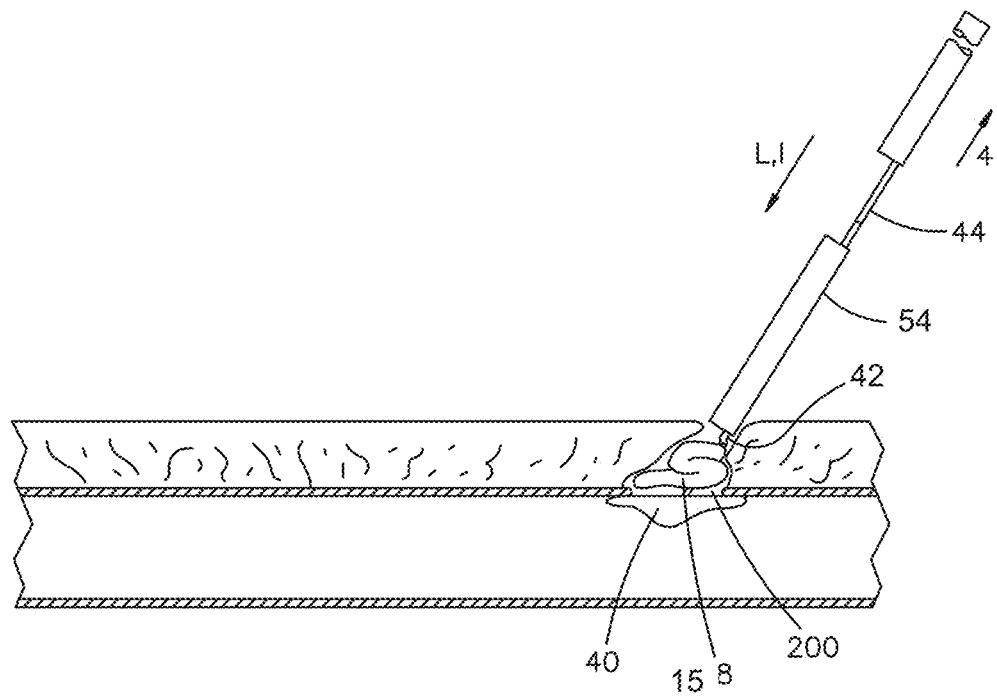
FIG. 11I is a schematic showing the locking member being tamped against the plug with a tamper.

After the user has pulled the suture 44 to cause tension in the suture 44 and to cause the plug 88 to enter the puncture site 200, the user advances the tamper 54 along the guide wire 15 and the suture 44 to lock the plug 88 in place. As shown in FIG. 11I, the tamper 54 contacts the locking member 42 and advances the locking member 42 along the suture 44 until the locking member 42 contacts the plug 88 and presses the plug 88 against an outer surface of the vessel. As the plug 88 is compressed by the tamper 54 the plug 88 folds over the top of and inside the puncture site 200 transitioning the sealing device 18 into a sealing configuration. It should be appreciated, however, that in some embodiments, the delivery component 26 is pulled such that the plug 88 is removed from the delivery component 26 within the release component 22 and the tamper 54 is employed within the release component 22. In such an embodiment, the release component 22 helps control the plug 88 as it is being tamped against the puncture site.

Figure 11J:
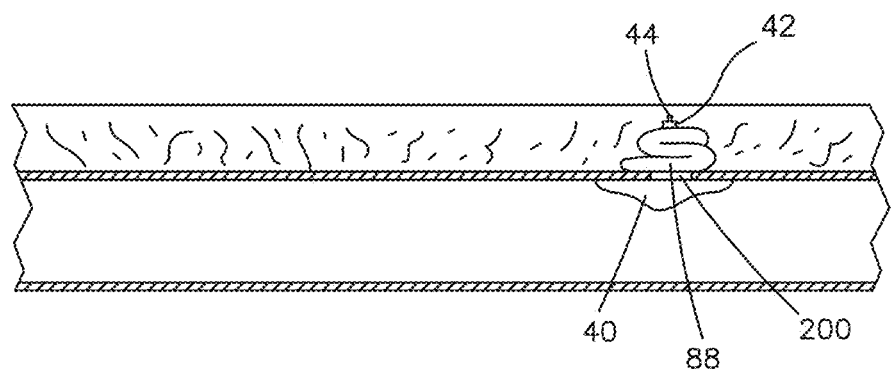

As shown in FIG. 11I, the locking member 42, together with the plug 88 and the toggle 40 are illustrated in the sealing configuration so as to affect a seal of the puncture site 200. As shown in FIG. 11I, tension is maintained on the suture 44 throughout the deployment of the plug 88 from the delivery component 26. After the puncture site 200 is sealed, the guide wire 15 can be removed as shown in FIG. 11J. As the guide wire 15 is removed, the suture 44 remains in tension and the user can re-compress the plug 88 with the tamper 54 as desired to confirm a proper seal of the puncture site 200. Once properly sealed, the suture 44 can be cut so that the remaining suture 44, tamper 54, and other components of the sealing device 18 can be removed from the puncture site 200, as shown in FIG. 11J. Remaining portions of the sealing device 18, including the toggle 40, plug 88, portion of suture 44, and locking member 42 (depending on material used) will resorb into the body of the patient over time.

Referring back to FIG. 11C, removal of the guide member 135 can minimize deployment forces on the plug 88 during deployment form the delivery component, which can minimize forces applied to the vessel wall when the plug 88 is locked in place against the vessel wall and toggle 40. Minimizing such deployment forces of the sealing device 18 also minimizes forces applied to the vessel wall along the puncture site. More specifically, during construction of the vascular closure device 12, the guide member 135 is centralized within the components of delivery assembly 14. As described above, after assembly but prior to use, the guide member 135 is disposed inside the delivery component 26 and also extends through the tamper 54, the plug 88, and the toggle 40 (when held in the insertion position between the release component 22 and the delivery component 26). It is believed that frictional forces between the guide member 135 and the compressed, pre-deployed plug 88 in the delivery component 26 hold the guide member 135 in place along the delivery assembly 14 and thus the vascular closure device 12. For instance, one or more assembly steps, including compression of the plug 88 within the delivery component 22 gently secure the guide member 135 in place. The frictional forces hold the guide member 135 as the vascular closure device 12 is positioned along the guide wire 15 and the guide wire 15 is inserted into the distal end of the guide member 135 and through the guide wire lumen to exit out the proximal end of the vascular closure device 12. However, the frictional forces can be overcome with a proximally directed force applied to the guide member 135. Once frictional forces are overcome, the guide member 135 may be removed from the sealing device 18 and delivery assembly 14 as is illustrated is FIG. 6C. For example, a user can pull on the proximal end of the guide member 135, which may extend from handle member, and carefully slide the guide member off the proximal-most end of the guide wire 15 used for the procedure. Removal of the guide member 135 before deploying the sealing device 18 (e.g. deploying the plug 88) reduces the forces required to deploy, or pull sealing device 18 from the delivery component, which directly reduces the forces that are necessarily applied to the vessel wall during sealing of the vessel puncture. Once the guide member 135 is removed from a portion of the sealing device, and more specifically the plug 88, more room is made available to the plug 88 to move within the delivery component 22 during deployment, thus the plug 88 likely has a lower volumetric compaction. With a lower volumetric compaction, the plug 88 will have a lower frictional engagement with the inner surface 81 of the delivery component 26. In addition, removal of the guide member 135 removes its additional surface area, which also interacts with and creates friction on the plug 88.

Figure 12A:
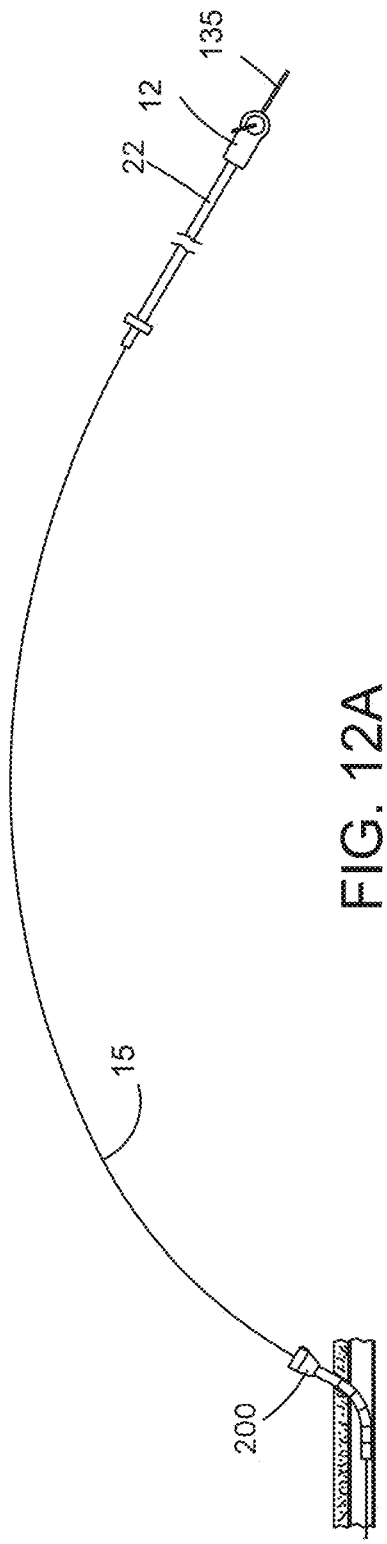
Figure 12B:
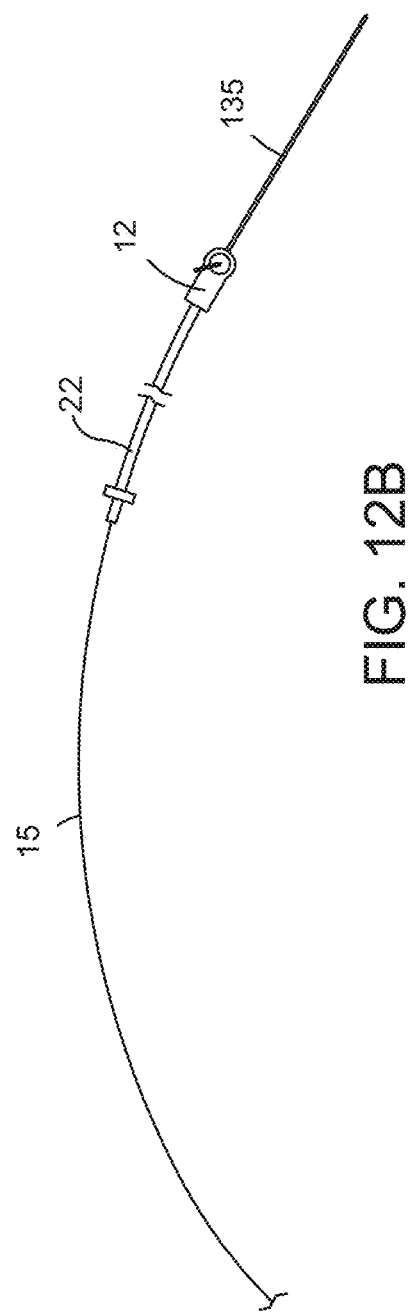

Embodiments of the present disclosure includes manual removal of the guide member 135 as described above and automatic removal of the guide member 135 from a portion of the sealing device 18. While manual removal is simple to accomplish, removal is also easy to forget. Referring FIGS. 12A-12D, automatic removal of the guide member 135 using a closed proximal end 104 is illustrated. Shown is the setting of a guide wire 15 passing from a vessel 204 through an access sheath 23, and external to a patient. Vascular closure device 12 may be advanced over the guide wire 15. As the guide wire encounters the closed-off end 104 of the guide member 135, further advancement as shown in FIG. 12B pushes the guide member 135 out of the closure device. This may be a relative movement: the guide wire 15 is free to be advanced within a stationary vascular closure device 12; or the vascular closure device 12, may be advanced over a stationary guide wire 15. Of importance if advancing the guide wire into the guide member 135 is to have sufficient guide wire length within the patient so as to prevent the inadvertent removal of the guide wire from the sheath and thus the puncture. Regardless of which component is moved, further relative motion pushes the guide member 135 completely out of the plug 88 and toggle 44, and then entirely out of the vascular closure device 12 as shown in FIG. 12C. When the guide member 135 has been removed from the vascular closure device 12, the guide member 135 may be easily slide off the guide wire 15 and discarded as shown in FIG. 12D. Once the vascular closure device 12 is mounted on the guide wire 15, the vascular closure device 12 is device may be slid proximally or distally as required to complete the procedure as described above with respect to FIGS. 11C-11I, so long as an end of the guide wire does not enter the device.

While the foregoing description and drawings represent the preferred embodiment of the present invention, it will be understood that various additions, modifications, combinations and/or substitutions may be made therein without departing from the spirit and scope of the present disclosure as defined in the accompanying claims. In particular, it will be clear to those skilled in the art that the present disclosure may be embodied in other specific forms, structures, arrangements, proportions, and with other elements, materials, and components, without departing from the spirit or essential characteristics thereof. One skilled in the art will appreciate that the present disclosure may be used with many modifications of structure, arrangement, proportions, materials, and components, which are particularly adapted to specific environments and operative requirements without departing from the principles of the present disclosure. In addition, features described herein may be used singularly or in combination with other features. For example, features described in connection with one component may be used and/or interchanged with features described in another component. The presently disclosed embodiment is therefore to be considered in all respects as illustrative and not restrictive, the scope of the present disclosure being indicated by the appended claims, and not limited to the foregoing description. It will be appreciated by those skilled in the art that various modifications and alterations of the present disclosure can be made without departing from the broad scope of the appended claims. Some of these have been discussed above and others will be apparent to those skilled in the art.

What is claimed:

1. A vascular closure device configured to be disposed along a guide wire toward a puncture of a vessel, the vascular closure device comprising:
   a sealing device configured to seal the puncture of the vessel, the sealing device including a toggle, a suture connected to the toggle, and a plug disposed along the suture, wherein the moveable guide member extends through at least one of the toggle and the plug;
   a delivery assembly that releasably holds the sealing device; and
   a moveable guide member supported by the delivery assembly, the moveable guide member being elongate along a longitudinal axis and that extends through at least a portion of the sealing device, the movable guide member including 1) a lumen that extends along the longitudinal axis and that is sized and configured to receive the guide wire as the vascular closure device is positioned along the guide wire, and 2) a gripping member that extends outwardly from the guide member, the gripping member being a tab, wherein a pulling force applied to the gripping member removes the moveable guide member from the sealing device.

2. The vascular closure device according to claim 1, wherein the moveable guide member includes at least one aperture.

3. The vascular closure device according to claim 2, wherein the at least one aperture is a plurality of apertures.

4. The vascular closure device according to claim 2, wherein the at least one aperture is an elongate slot.

5. The vascular closure device according to claim 1, wherein the movable guide member includes a guide body, the guide body defining a closed proximal end and a distal end spaced from the closed proximal end along the longitudinal axis.

6. The vascular closure device according to claim 5, wherein the moveable guide member is removed from the at least a portion of the sealing device when 1) the lumen receives the guide wire, and 2) a proximal-most end of the guide wire abuts the closed proximal end the guide body.

7. The vascular closure device according to claim 5, wherein the closed proximal end includes a proximal wall that extends at least partially along a transverse direction that is perpendicular to the longitudinal axis.

8. The vascular closure device according to claim 7, wherein the proximal wall defines at least one aperture that extends along the longitudinal axis.

9. The vascular closure device according to claim 5, wherein the guide body defines a side wall that extends around the longitudinal axis, the side wall defining at least one aperture that extends through the sidewall.

10. The vascular closure device according to claim 1, further comprising at least one actuator, the at least one actuator configured to cause the removal of the moveable guide member from within the at least a portion of the sealing device.

11. The vascular closure device according to claim 10, wherein the delivery assembly includes a front end and a rear end spaced from the front end in a proximal direction, wherein the at least one actuator is configured to translate the moveable guide member in the proximal direction to remove the moveable guide member from the at least a portion of the sealing device.

12. The vascular closure device according to claim 11, further comprising a gear assembly that is operably coupled to the at least one actuator, wherein actuation of the at least one actuator causes the gear assembly to translate the moveable guide member in the proximal direction to remove the moveable guide member from the at least a portion of the sealing device.

13. The vascular closure device according to claim 1, further comprising at least one actuator that is configured to cause the delivery assembly to transition the toggle from an insertion position where the toggle is held in place by the delivery assembly into a released position where the toggle is moveable relative to the delivery assembly.

14. The vascular closure device according to claim 13, wherein the at least one actuator has a first actuation phase that removes moveable guide member from the at least a portion of the sealing device, and a second actuation phase that causes the delivery assembly to transition the toggle from the insertion position into the released position.

15. A vascular closure device configured to be disposed along a guide wire toward a puncture of a vessel, the vascular closure device comprising:
   a sealing device configured to seal the puncture of the vessel, the sealing device including a toggle, a suture connected to the toggle, and a plug disposed along the suture;
   a delivery assembly including a front end and a rear end spaced from the front end in a proximal direction, the front end of the delivery assembly releasably holding the sealing device;
   a moveable guide member supported by the delivery assembly and that extends through at least one of the toggle and the plug in the first position, the movable guide member including a distal end, a proximal end spaced from the distal end in the proximal direction, a lumen that extends from the distal end toward the proximal end in the proximal direction and is sized to receive a guidewire, and a gripping member that extends relative to the movable guide member,
   wherein a pulling force applied to the gripping member causes the movable guide member to translate relative to the delivery assembly and via at least one actuator from a first position where the movable guide member extends through the at least a portion of the sealing device to a second position where the movable guide member does not extend through the at least a portion of the sealing device.

16. The vascular closure device according to claim 15, wherein the movable guide member is configured to be removed entirely from the delivery assembly.

17. The vascular closure device according to claim 15, wherein the delivery assembly defines a first length that extends from the rear end to the front end, and the movable guide member defines a second length that extends from the proximal end to the distal end, wherein the second length is greater than the first length.

18. The vascular closure device according to claim 15, further comprising a handle member, wherein in the first position the movable guide member extends through the handle member and through the at least a portion of the sealing device, and in the second position the movable guide member is removed from the at least a portion of the sealing device.

19. The vascular closure device according to claim 15, wherein the moveable guide member extends through a passage in the plug, and the moveable guide member is configured to translate in the proximal direction so as to be removed from the passage of the plug.

20. The vascular closure device according to claim 15, wherein the moveable guide member includes at least one aperture.

21. A method for sealing a puncture of a vessel, the method comprising the steps of:
   positioning a guide member that extends through at least a portion of a sealing device along a guide wire such that a proximal end of a guide wire enters a lumen of the guide member, wherein a delivery assembly supports the guide member and releasably holds the sealing device;
   advancing the guide member and the sealing device along the guide wire in a distal direction until the sealing device is advanced through the puncture of the vessel;
   pulling a gripping member of the guide member relative to the delivery assembly in a proximal direction that is opposite to the distal direction so as to remove the guide member from the at least a portion of the sealing device.

22. The method of claim 21, further comprising deploying the sealing device from the delivery assembly while maintaining the relative position of the guide wire with respect to the sealing device.

23. The method of claim 21, wherein sealing device includes a plug disposed along a filament, wherein the guide member extends through the plug, wherein moving the guide member includes removing the guide member from the plug.

24. The method of claim 21, wherein sealing device includes a toggle attached to the filament in the distal direction relative to the plug, wherein the guide member extends through the plug and the toggle, wherein the step of moving the guide member includes removing the guide member from the toggle and the plug.

25. The method of claim 21, wherein pulling the gripping member of the guide member includes removing the guide member entirely from the delivery assembly.

26. The method of claim 21, further comprising moving the guide member from the at least a portion of the sealing device via an actuator.

* * * * *